United States Patent
Kilroy et al.

(10) Patent No.: US 10,842,577 B2
(45) Date of Patent: Nov. 24, 2020

(54) HYPERDEXTEROUS SYSTEM USER INTERFACE

(71) Applicant: SRI International, Menlo Park, CA (US)

(72) Inventors: Pablo Eduardo Garcia Kilroy, Menlo Park, CA (US); Seungkook Yun, San Jose, CA (US); Karen Shakespear Koenig, San Jose, CA (US); Joan Savall, Palo Alto, CA (US)

(73) Assignee: SRI International, Menlo Park, CA (US)

( * ) Notice: Subject to any disclaimer, the term of this patent is extended or adjusted under 35 U.S.C. 154(b) by 429 days.

(21) Appl. No.: 15/553,543

(22) PCT Filed: Jul. 30, 2015

(86) PCT No.: PCT/US2015/042991
§ 371 (c)(1),
(2) Date: Aug. 24, 2017

(87) PCT Pub. No.: WO2016/137527
PCT Pub. Date: Sep. 1, 2016

(65) Prior Publication Data
US 2018/0036088 A1    Feb. 8, 2018

Related U.S. Application Data

(60) Provisional application No. 62/120,128, filed on Feb. 24, 2015.

(51) Int. Cl.
*A61B 34/37* (2016.01)
*A61B 34/00* (2016.01)
(Continued)

(52) U.S. Cl.
CPC .............. *A61B 34/37* (2016.02); *A61B 34/30* (2016.02); *A61B 34/74* (2016.02); *G06F 3/011* (2013.01);
(Continued)

(58) Field of Classification Search
CPC ......... A61B 34/37; A61B 34/30; A61B 34/74; A61B 2034/741; A61B 2017/00207; G05B 19/00
(Continued)

(56) References Cited

U.S. PATENT DOCUMENTS

| | | | |
|---|---|---|---|
| 5,784,542 A * | 7/1998 | Ohm | B25J 3/04 700/247 |
| 6,364,888 B1 * | 4/2002 | Niemeyer | H04N 13/327 606/130 |

(Continued)

FOREIGN PATENT DOCUMENTS

| | | |
|---|---|---|
| CN | 1155833 A | 7/1997 |
| CN | 1243690 A | 2/2000 |

(Continued)

OTHER PUBLICATIONS

Chinese Office Action dated Feb. 28, 2019 for related Chinese Appln. No. 201580078264.I 9 Pages.
(Continued)

*Primary Examiner* — Jason Holloway
(74) *Attorney, Agent, or Firm* — McDonnell Boehnen Hulbert & Berghoff LLP

(57) ABSTRACT

Systems and methods for embodiments of a hyperdexterous robotic system using groundless user input devices (UIDs). In some embodiments, the hyperdexterous system allows for the slave control to follow the master control even when the two are misaligned. The motion of the master control occurring in multiple degrees of freedom may be decoupled (Continued)

into its component parts and processed differently. Each degree of freedom may be processed independently and scaled differently. For example, in some embodiments, only the roll motion of the groundless user interface device is transferred, in some embodiments, the master slave control is only allowed when the master and slave are within a certain region of each other.

22 Claims, 20 Drawing Sheets

(51) Int. Cl.
  *A61B 34/30*   (2016.01)
  *G06F 3/01*   (2006.01)
  *A61B 17/00*   (2006.01)
  *G05B 19/00*   (2006.01)

(52) U.S. Cl.
  CPC .... *G06F 3/017* (2013.01); *A61B 2017/00207* (2013.01); *A61B 2034/741* (2016.02); *G05B 19/00* (2013.01)

(58) Field of Classification Search
  USPC ........................................................ 700/245
  See application file for complete search history.

(56) References Cited

U.S. PATENT DOCUMENTS

| | | | | |
|---|---|---|---|---|
| 8,282,653 | B2* | 10/2012 | Nelson | A61B 34/30 606/130 |
| 9,901,411 | B2* | 2/2018 | Gombert | A61B 34/30 |
| 2006/0142657 | A1* | 6/2006 | Quaid | A61B 17/1764 600/424 |
| 2008/0248871 | A1* | 10/2008 | Szturm | G06F 3/0346 463/36 |
| 2009/0240259 | A1* | 9/2009 | Nelson | A61B 34/30 606/130 |
| 2009/0301160 | A1* | 12/2009 | Baumgarten | B21D 19/043 72/306 |
| 2011/0118753 | A1* | 5/2011 | Itkowitz | G06F 3/014 606/130 |
| 2012/0071892 | A1 | 3/2012 | Itkowitz et al. | |
| 2014/0277741 | A1* | 9/2014 | Kwon | B25J 9/1689 700/263 |
| 2015/0018841 | A1* | 1/2015 | Seo | A61B 34/77 606/130 |
| 2015/0038982 | A1 | 2/2015 | Kilroy et al. | |
| 2017/0055940 | A1* | 3/2017 | Shoham | A61B 8/0841 |

FOREIGN PATENT DOCUMENTS

| | | | |
|---|---|---|---|
| CN | 1457747 | A | 11/2003 |
| CN | 1669532 | A | 9/2005 |
| CN | 102646275 | A | 8/2012 |
| CN | 103870026 | A | 6/2014 |
| CN | 103995592 | A | 8/2014 |
| CN | 104252225 | A | 12/2014 |
| DE | 102013110847 | B3 * | 1/2015 |
| EP | 3262469 | A1 | 1/2018 |
| JP | 2013-510671 | | 3/2013 |
| KR | 10-2017-0140179 | A | 12/2017 |
| WO | 2016/137527 | A1 | 9/2016 |

OTHER PUBLICATIONS

Japanese Office Action dated May 28, 2019 for related Japanese Patent Application No. 2017-544633 6 Pages.
Chinese Office action dated Sep. 17, 2019 for related Chinese appln. No. 201580078264.1.
Extended European Search Report, dated Jul. 25, 2018, for EP application No. 15883617.1.
Written Opinion of the International Search Authority dated Nov. 2, 2015 for WO Application No. PCT/US15/042991.
Outgoing—ISA/210—International Search Report dated Nov. 2, 2015 for WO Application No. PCT/US15/042991.
(IPEA/409) International Preliminary Report on Patentability Chapter II or (IB/373) International Preliminary Report on Patentability Chapter I dated Sep. 8, 2017 for WO Application No. PCT/US15/042991.
Third Office Action of the China National Intellectual Property Administration dated Mar. 9, 2020, for related Chinese Patent Application No. 201580078264.1.

* cited by examiner

Unclutched state

Clutched state

HYPERDEXTEROUS SYSTEM USER INTERFACE

CROSS-REFERENCE TO RELATED APPLICATIONS

This application is a U.S. National Stage Application under 35 U.S.C. § 371 of International Application No. PCT/US2015/042991, filed on Jul. 30, 2015, which claims the priority and benefit under 35 U.S.C. § 119(e) of U.S. Provisional No. 62/120,128, filed Feb. 24, 2015, all of which are hereby incorporated by reference in their entirety and should be considered a part of this specification.

BACKGROUND OF THE DISCLOSURE

Field of the Disclosure

The present application relates generally to hyperdexterous robotic systems, such as for performing surgical operations.

Description of the Related Art

The use of robotics in surgery is becoming increasingly common. In such robotic systems, typically an operator such as a surgeon operates a control called the master control. The movements of the master control are then reproduced on a slave system, which may be used to control one or more surgical tools or instruments. Thus, the surgeon may perform surgical operations on a patient by manipulating the master control, causing corresponding movements to be performed by the surgical tools at the slave control.

SUMMARY OF VARIOUS EMBODIMENTS

Embodiments of systems and methods disclosed herein disclose hyperdexterous robotic systems using groundless user input devices (UIDs). An operator, such as a surgeon performing a surgical operation, operates a master control in order to cause corresponding movements to be performed by robotics tools of a slave system. Because the master control uses groundless UIDs, the operator may operate the master controls in free space from any appropriate position. However, because the operator's movements are not constrained or oriented by a user console, the groundless UIDs' orientations with respect to the user's eye frame may become misaligned with the robotic tools with respect to the camera frame as displayed to the user in the live video feed of the slave system. The live video feed may be at an arbitrary orientation and position relative to the slave system. Thus, there may be a need to match the UID frame with respect to the user's eye frame and the robot tool frame with respect to the camera frame.

In some embodiments, the hyperdexterous system allows for the slave control to follow the master control even when the two are misaligned. For example, in at least one embodiment, only the roll motion of the groundless user interface device is transferred. In some embodiments, the master-slave control is only allowed when the master and slave are within a certain region of each other.

In some embodiments, the motion of the master control occurring in multiple degrees of freedom is decoupled into its component parts and processed differently. Each degree of freedom can be then processed independently and scaled differently. In some embodiments, anisotropic scaling may be implemented, where the motion of the groundless user interface device is scaled differently depending on the state of the user interface device and the robotic tool it controls.

In some embodiments, because the hyperdexteroes system may not necessarily have a console at which an operator is forced to sit in order to control the robotic system, a center of workspace is defined. The center of workspace may be a region in space that the operator can identify and return to in order to orient himself or herself. Using this center of workspace, a natural coordinate system is defined which transforms natural movements of the human operator to specific movements of the robotic tool. The natural coordinate system frilly be defined with respect to the body of the operator, including one more body parts of the operator, such as an eye or an eye angle, a hand, a torso, and/or the like.

In one embodiment, a system is disclosed. The system may include a first robotic tool and a first groundless user interface device (UID) for use by an operator and configured to control the first robotic tool using a first frame of reference, the control comprising identifying a first UID motion of the first UID and performing a first robotic tool movement of the first robotic tool based at least in part upon the identified first UID motion of the first UID. The system may further include a second robotic tool and a second groundless user interface device (UID) for use by the operator and configured to control the second robotic tool using a second frame of reference independent of the first frame of reference, the control comprising identifying a second UID motion of the second UID and performing a second robotic tool movement of the second robotic tool based at least in part upon the identified second UID motion of the second UID.

In some embodiments, the system may include one or more of the following. The first robotic tool may comprise at least one of a grasper, a surgical tool, or a camera. The first UID may be further configured to be controlled by a first hand of the operator and the second UID is further configured to be controlled by a second hand of the operator. Controlling the first tool may further comprise: determining that a drive has been engaged; and in response to determining that the drive has been engaged, establishing a position on a first forearm of the operator associated with the first hand, wherein a UID motion of the first UID is measured in relation to the position on the first forearm. Controlling the first robotic tool may further comprise: comparing an orientation of the first UID with respect to a first coordinate frame with an orientation of the first robotic tool with respect to a second coordinate frame, wherein the first controls the first robotics tool if the orientation of the first UID with respect to the first coordinate frame is within a certain region relative to the first robotic tool with respect to the second coordinate frame. The first coordinate frame may correspond to a natural coordinate frame associated with the operator, and the second coordinate frame corresponds to a camera frame associated with the first robotic tool. The region may comprise a cone around the first robotic tool, the cone comprising a vertex corresponding to an end of the first robotic tool. A speed of the first robotic tool movement of the first robotic tool may be adjusted based at least in part upon a calculated difference between the orientation of the first UID relative to the first robotic tool. The first robotic tool may be associated with a plurality of control schemes associated with a plurality of different regions, and wherein one of the plurality of control schemes used by the first UID to control the first robotic tool is based at least in part upon the orientation of the first with respect to the first coordinate frame relative to the orientation of the first robotic tool with respect to the second coordinate frame.

In another embodiment, a system is disclosed. The system may include a first robotic tool and a first groundless user interface device (UID) configured to control the first robotic tool using a first frame of reference, the control comprising identifying a first UID motion of the first UID, decoupling the first UID motion into two or more components comprising at least a first component and a second component, performing a first transformation on the two or more components, wherein the first component and the second component are transformed differently, and performing a first robotic tool movement of the robotic tool based at least in part upon the first transformation.

In some embodiments, the system may include one or more of the following. The two or more components may comprise at least a roll component, a pitch component, and a yaw component, and the first transformation comprises transforming the roll component to the performed first robotic tool movement of the first robotic tool, but not the pitch component or the yaw component, in response to a determination that the identified first UID motion satisfies an established criteria. The two or more components may comprise at least a roll component, a pitch component, and a yaw component, and the first transformation comprises: performing an intermediate transformation on the yaw component and the pitch component, wherein the intermediate transformation generates a modified yaw component, a modified pitch component, and an intermediate roll component; and determining a modified roll component, the modified roll component based at least in part upon a sum of the roll component and the intermediate roll component obtained from the intermediate transformation, wherein the first robotic tool movement of the first robotic tool is based at least in part upon one of the modified roll component, modified yaw component, or modified pitch component. The two or more components may comprise at least a rotational component and a translational component, and wherein the first transformation comprises: automatically determining whether the translational component satisfies a threshold, and setting a translational component for the first robotic tool movement of the first robotic tool to 0, if the translational component does not satisfy the threshold; and automatically determining whether the rotational component satisfies a threshold, and setting a rotational component for the first robotic tool movement of the first robotic tool to 0, if the rotational component does not satisfy the threshold. The first transformation may comprise scaling at least one component of the two or more components, and wherein an amount of scaling is based at least in part upon a position of the first UID. The first UID may comprise a UID configured to be held by an operator, such that a position of the UID is based at least in part upon a wrist position of the operator, a range of motion of the wrist of the operator being partitioned into at least a comfortable region and an uncomfortable region, and wherein the amount of scaling is based at least in part upon which region the wrist is in. The first UID may control the first robotic tool only if the first UID is located within a natural workspace region. Controlling the first robotic tool may further comprise: determining that a drive has been engaged; determining that the first UID is within the natural workspace region; and in response to determining that the drive has been engaged and that the first is within the natural workspace, establishing a zero position for the first corresponding to a position of the first robotic tool.

In yet another embodiment, a computer-implemented method is disclosed. The method may implemented by one or more computing devices configured with specific computer-executable instructions to include identifying a motion of at least one groundless user interface device (UID), decoupling the identified motion into two or more components, comprising at least a first component and a second component, performing at least one transformation on the two or more components, wherein the first component and the second component are transformed differently, and performing a movement of at least one robotic tool, wherein the movement is based at least in part upon the at least one transformation performed on the first component and the second component.

In some embodiments, the computer-implemented method may be implemented using one or more of the following. The at least one robotic tool may comprise at least one of a grasper, a surgical tool, or a camera. The at least one UID may comprise a first UID and a second UID, the first and second UIDs configured to be controlled by a first hand and a second hand of an operator, and wherein the first and second UIDs may be moved by the first and second hands in independent coordinate frames. The computer-implemented method may further comprise: comparing an orientation of the at least one UID with an orientation of the at least one robotic tool in a particular coordinate frame, wherein the at least one UID controls the at least one robotics tool if the orientation of the least one UID is within a certain region relative to the at least one robotic tool in the coordinate frame. A speed of the movement of the at least one robotic tool may be adjusted based at least in part upon a calculated difference between the orientation of the at least one UID relative to the at least one robotic tool.

DESCRIPTION OF EMBODIMENTS

Overview

Figure 1:
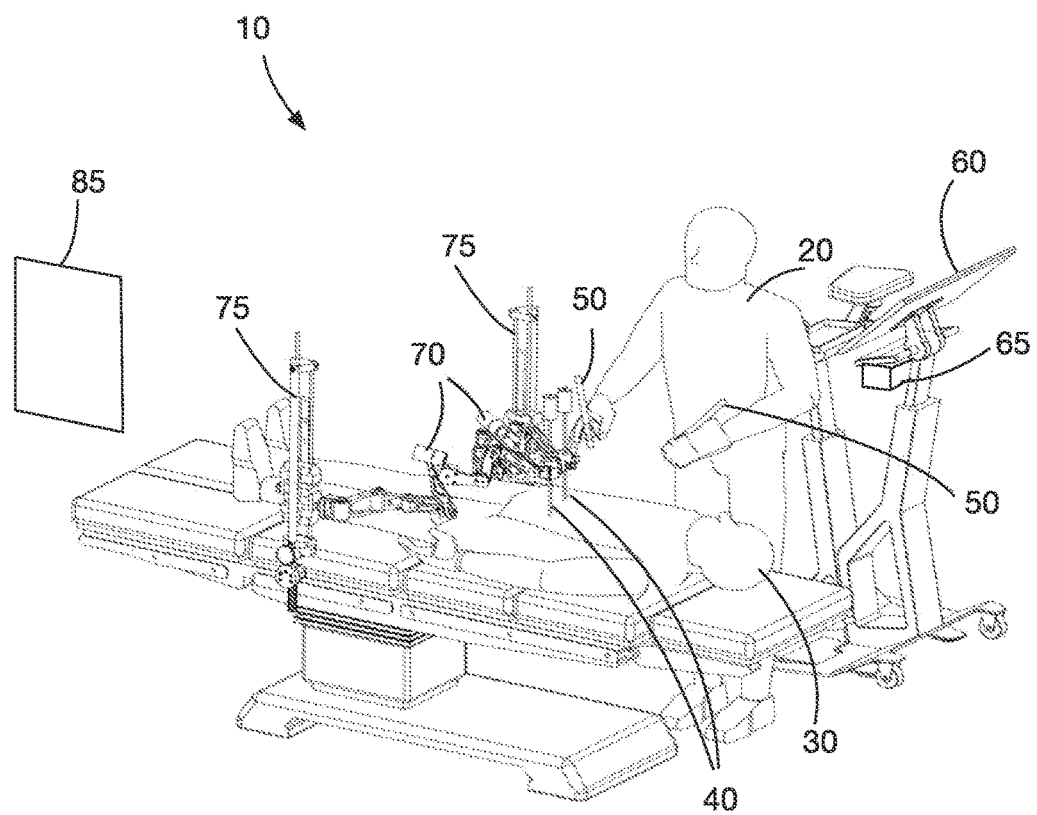
FIG. 1 illustrates a hyperdexterous surgical system, in accordance with some embodiments.

Although certain embodiments and examples are disclosed below, additional subject matter extends beyond the specifically disclosed embodiments to other alternative embodiments and/or uses and to modifications and equivalents thereof. Thus, the scope of the disclosure is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manlier that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Although the disclosure will refer primarily to robotic systems used for surgery or other medical operations for purpose of example, the methods and systems described herein may be applied to any type of hyperdexterous robotic systems.

The use of robotics in surgery is becoming increasingly common. In such robotic systems, typically an operator such as a surgeon operates a control called the master control. The movements of the master control are then reproduced on a slave system. Typically, in such systems the master control is coupled to a console at which the surgeon may sit or stand. The coupling between the console and the master control is such that while movements in several degrees of freedom may be allowed, the console and the master control cannot be detached. These types of master controls are typically called grounded controls. In this type of arrangement, the surgeon uses the console to orient himself or herself. Because the master control input devices and the displayed video feed of the slaved instruments are aligned, the surgeon's hand movements are faithfully reproduced by the slaved instruments. However, while such systems allow the surgeon to perform complex surgeries, the surgeon is constrained to a position quite often many feet away from the patient and slave robot system in order to accommodate a console which enforces this alignment between the displayed video feed of the slave robot tools and the master input devices.

Embodiments of the systems and methods described herein disclose a robotic system that allow a surgeon to perform surgery with robotic and manual tools (such as laparoscopic tools), wherein the surgeon is able to position himself or herself in an advantageous position in relation to the patient. The surgeon may operate the robotic tools through the use of groundless user interface devices. Groundless devices, in contrast to the grounded devices, may be manipulated in free space. Groundless devices may be wired, wireless, or groundless, and provide the ability for the surgeon to perform the surgical procedures from any appropriate position. For example, the surgeon may assume a position near the bed so that robotic or manual surgery may be performed. In addition, better communication between the surgeon and the medical staff may be enabled, as the surgeon does not need to be remote from the patient. Embodiments of a hyperdexterous surgical system are disclosed in U.S. patent application Ser. No. 14/388,180, titled "Hyperdexterous Surgical System," filed on Sep. 25, 2014, U.S. patent application Ser. No. 14/510,465, titled "Hyperdexterous Surgical System," filed on Oct. 9, 2014, U.S. patent application Ser. No. 14/510,474, titled "Hyperdexterous Surgical System," filed on Oct. 9, 2014, and U.S. patent application Ser. No. 14/510,566, titled "Hyperdexterous Surgical System," filed on Oct. 9, 2014, and all such applications are hereby incorporated by reference herein in their entirety and should be considered a part of this specification. In addition, embodiments of user interface devices and related systems are disclosed in U.S. Provisional Patent Appl. No. 62/151,596, titled "Hyperdexterous Surgical System User Interface Devices," filed on Apr. 15, 2015, which is hereby incorporated by reference herein in its entirety and should be considered a part of this specification.

However, new paradigms and new ways of controlling the system in order to implement groundless devices may be beneficial. One such benefit of some embodiments is fueled by not needing the surgeon to be at a user console. As mentioned above, grounded devices typically use the console as a way to orient the surgeon. Since the console is a physical device, it also provides the surgeon a place to rest his or her arm while operating the master console, which again is useful in the providing orientation. While operating with groundless devices in free space, the orientation reference does not exist anymore. In these circumstances, requiring perfect alignment between the master input devices and live feed of the slave motions may make the system harder to operate. Thus, there is a need to allow the system to operate even if the master controls and slave video feed are misaligned within certain bounds. In contrast, systems that use grounded devices typically do not allow the operation when the master input devices and slave video feed are misaligned. Additionally, it may be beneficial to provide cues to the user related to the orientation of the physical slave robotic tools versus the orientation of the displayed video feed of the slave robotic tools in order to aid the user in operating both a manual tool, such as a laparoscopic tool, and a robotic master input device simultaneously. As one example, the cues may be provided by rendering a series of interpolated frames that illustrate the three dimensional motion of "zooming" from the user's eye coordinate frame to the coordinate frame of the camera held by the slave robot.

In another aspect of some embodiments, returning back to systems using grounded devices, the physical nature of the user interface console often force the motion of the surgeon's hands in certain ways. In systems where the control of the system may be achieved through groundless user input devices, the motion of the surgeon's hand is not constrained. In some cases, the unconstrained motion may lead to undesirable motion. As an example, the wrist of a human (such as a surgeon) moves in six degrees of freedom (DOF). These DOFS are roll, pitch, yaw, movement in the X direction, movement in the Y direction, and movement in the Z direction, assuming that a rectilinear coordinate system is associated with the wrist. The elbow and the shoulder may provide additional DOES. However, for this example, they may be ignored. As the surgeon clutching a groundless input device moves his or her wrist to perform a roll operation, it is a natural tendency of the wrist to also move in other degrees of freedom, which may not be desired, in these circumstances, it may be beneficial in some embodiments to decouple or scale the motions in the various DOFs the slave is commanded to go though. Thus, there may be a benefit in some embodiments to decoupling or scaling the motion of the slave differently in each DOF it can go through so that some motions of the master are emphasized and some are deemphasized. In a related aspect, there may be a further benefit in some embodiments to establish which degrees of freedom to emphasize and which ones to deemphasize. Thus, embodiments of the system may establish a situation dependent hierarchy of emphasis. For example, in one configuration, the surgeon may find it easier to apply a rolling motion than to apply a pitch and yaw motion; in addition, the surgeon may find it easier to apply a pitch and yaw motion than to apply a translation motion. This type of hierarchy may improve the ease of use when groundless UIDs are utilized.

In some embodiments, the ability of the surgeon to operate the user input device in air instead of at a console establishes yet another need. As described above, in systems with grounded devices, the surgeon uses the console as a means for orientation. With groundless UIDs, there may not be a similar physical structure that can provide this type of orientation. While a groundless UID associated with a physical structure, for example an armrest or a chair, the groundless UIDs may not be mechanically constrained to move only in a prescribed region. Thus, in some embodiments, it may be beneficial to create a home workspace in the space around the user that feels natural for the user to return to. If the surgeon is unsure about the relationship between his or her hands and the slaved robotic tool, by returning to the home workspace, reorientation may be obtained.

Several approaches are described in this disclosure. In one embodiment, instead of a system that requires that the master and the displayed image of the slave robot, sometimes referred to as the slave control, be aligned, the hyperdexterous system allows for the slave control to follow the master control even when the two are misaligned. Several variations and embodiments of this concept are described. In one embodiment, only the roll motion of the groundless user interface device is transferred. In another embodiment, the master slave control is only allowed when the master and slave are within a certain region, or multiple regions, of each other. For example, the multiple regions may include a region centered around 0 degrees misalignment and another centered around 180 degrees misalignment (about the roll axis). In yet other embodiments, the motion of the master control occurring in multiple degrees of freedom is decoupled into its component parts and processed differently. Each degree of freedom can be then processed independently and scaled differently. Variations and embodiments of this concept may include anisotropic scaling, where the motion of the groundless user interface device is scaled differently depending on the state of the user interface device and the robotic tool it controls. In yet other embodiments, because the hyperdexterous system may not necessarily have a console at which an operator is forced to sit in order to control the robotic system, a center of workspace is defined. This center of workspace is a region in space that the operator can identify and return to in order to orient himself or herself. Using this center of workspace concept, and in yet further concepts, a natural coordinate system is defined which transforms natural movements of the human operator to specific movements of the robotic tool.

Description of the Figures

FIG. 1 illustrates a hyperdexterous system 10, in accordance with some embodiments. As illustrated in the figure, an operator 20, such as a surgeon, operates on a patient 30 with robotically controlled tools 40. The robotically controlled tools are controlled by groundless user interface devices (UID) 50. In some embodiments, the robotic tools 40 are held by motorized jointed arm 70 which are coupled to the bed via passive arms 75. In some embodiments, the arms are passive, whereas in other embodiments, the arms are active. For example, the motorized jointed arm 70 may be coupled to the bed via active arms.

In the illustrated figure, a user interface stand 60 is behind the operator, although it is understood that in other embodiments, user interface stand 60 may be positioned in other locations relative to the operator, or may be absent entirely. The operator is not required to be in the vicinity of the user interface stand 60. Instead, the operator may position himself or herself in an optimal position in relation to the patient and manipulate the robotic tools 40 via the groundless user interface devices 50.

Figure 18:
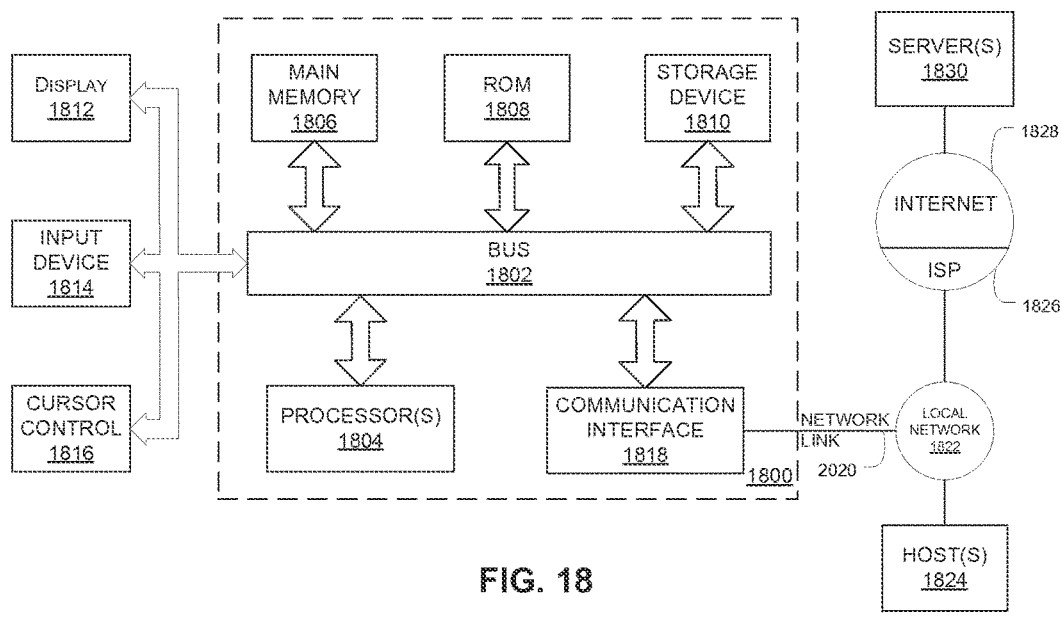
FIG. 18 illustrates an embodiment of a computer system with which certain systems and methods discussed herein may be implemented.

In some embodiments, the system 10 can enable the surgeon to use robotic tools or manual toots or both during a procedure due to the proximity to the patient. If the surgeon wishes to use robotic tools, then he or she may use the groundless UIDs 50 to control the toots. The system 10 translates the surgeon's hand movements into movements of the robotic tools thus enabling him or her to perform surgeries. Various types of robotic tools may be used, such as, but not limited to graspers and staplers. Robotic tools may also include cameras. With the help of these cameras, the surgeon may visualize the organs and the tools inside the body to perform the surgery. In some embodiments, the manipulation of the robotic tools via the groundless UIDs are comprehendible and feel natural to the surgeon. The surgeon may use multiple visual cues to comprehend the motion of the robotic tools inside the patient's body. These visual cues may include, but are not limited to, images of the organs and the tools as seen by the camera and displayed on a monitor 85, the position of the surgeon with respect to the patient, and the position and orientation of the visible portions of the tool that are outside the patient's body. As an example, if the surgeon moves left and right with his or her hands, to aid in the surgeon's understanding, the tools may also move left and right on the monitor 85. As another example, if the surgeon moves his or her hands up and down, the tools may also move up and down on the monitor 85. Various types of associations other than the examples above between hand movements and how they are displayed on the monitor are possible and may be selectable or settable according to user preference or other means. To make these associations, a computer associated with system 10 (not shown in FIGS. 1 and 2) transforms the motions of the user's hands to that of the robotic tools. In some embodiments, the computer may be a computer system as illustrated in FIG. 18, described further below.

Figure 2:
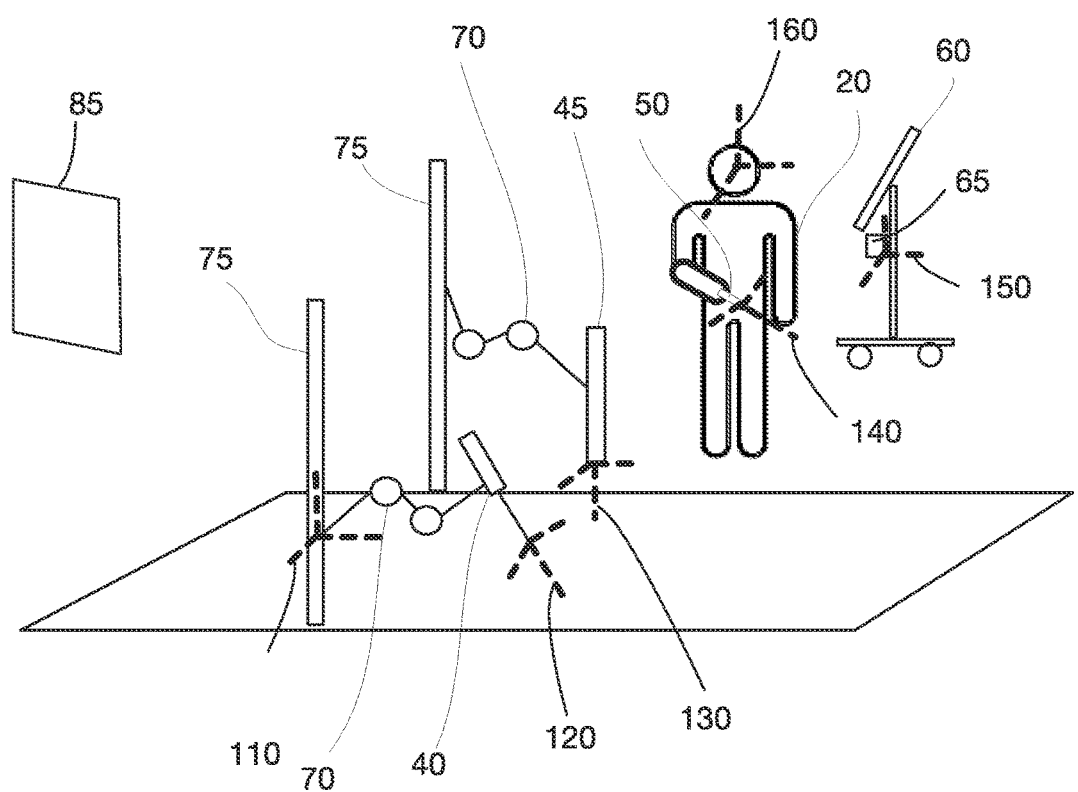
FIG. 2 illustrates a hyperdexterous surgical system showing coordinate frames, in accordance with some embodiments.

In some embodiments, these transforms require that coordinate frames be associated with one or several sensors of the system 10. A coordinate frame may be thought of as a coordinate system that defines the orientation of the body the frame is associated with respect to a reference frame. For example, FIG. 2 illustrates coordinate frames that may be associated with a hyperdexterous system 10, in accordance with some embodiments. In FIG. 2, coordinate frames are shown as 110, 120, 130, 140, 150 and 160 associated with the passive arm 75, the robotic tool 40 (which may be a grasper, as an example), the camera 45, the groundless UID 50, an user interface device base 65, and the eyes of the surgeon 20 respectively. Other sensors of system 10 may also be used to define the various coordinate frames. The UID base 65 is a sensor that receives the groundless signals from the groundless UIDs 50 and converts the location of these. UIDs into spatial coordinates relative to a frame associated with it. Thus, one of the tasks of the computer associated with system 10 is to convert the motions the operator makes into motions of the robotic tools in a way that the operator can understand and comprehend.

One technique to achieve the comprehension is to align the master control or the control that the operator uses and the robotic tool that is controlled by the master control. More specifically, the system can align (a) the UID frame with respect to the operator's eye frame and (h) the robotic tool frame with respect to the camera frame that has captured the robotic tool motion. Generally, these types of control systems are called master-slave control systems where the slave (in this case the robotic tool) faithfully follows the motions of the master. For example, the operator uses the console and manipulates the master control which is electromechanically coupled to the console, as a way to orient himself or herself. However, in some embodiments, such as system 10 as illustrated in FIG. 1, that type of visual cue and/or mechanical constraint is not necessarily present as the operator may be using the groundless UIDs. Thus in some embodiments, misaligned motion is permitted. In some embodiments, the master control and robotic tool may be considered to be misaligned when an orientation of a groundless UID relative to an eye frame of the operator is not aligned with an orientation of a robotic tool controlled by the groundless UID with respect to a camera frame depicting the robotic tool (for example, the camera frame in a video feed being presented to the operator).

Various embodiments of methods may be used to decouple or de-emphasize unwanted motion. To explain this further with a specific example, when a rolling motion is performed by an operator with his or her hands, there is a tendency for the hand to also undergo a translatory motion, simply due to the mechanics of the hand. This translatory motion may be undesired and unwanted. In these cases, it may be advantageous n some embodiments to suppress or remove the translatory motion. More generally, when an operator such as a surgeon is manipulating a groundless UID, in many situations there may be undesired or unwanted coupled motion. Unlike UIDs that have physical constraints, the groundless UID cannot force the operator to decouple such motions. Thus, it may be desirable in some embodiments to be able to suppress or remove this coupled motion. These and other concepts are explained in detail below. However, to better understand the concepts, embodiments of coordinate frames associated with system 10 are now explained in detail below.

Coordinate Frames

Figure 3:
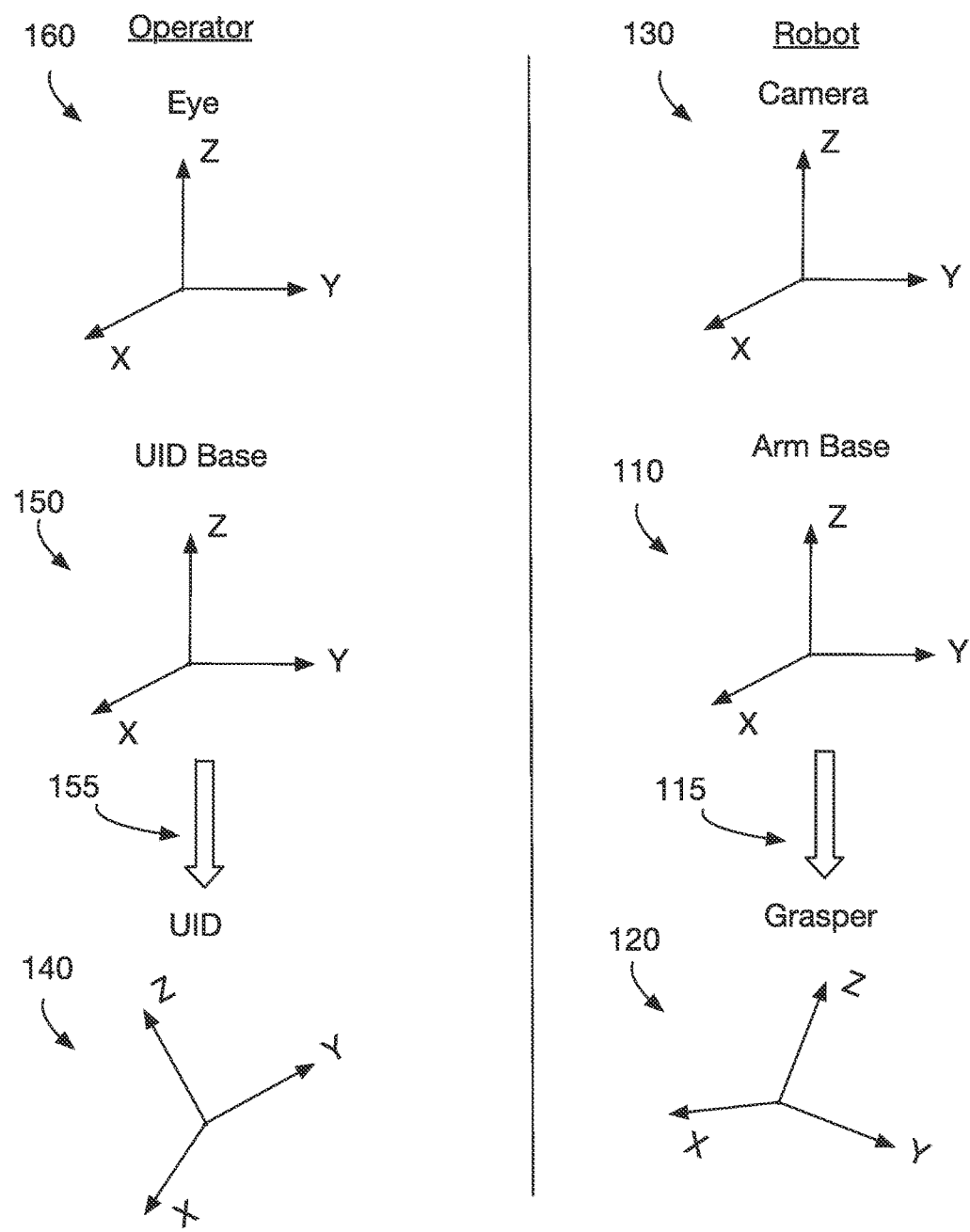
FIG. 3 illustrates the various coordinate frames of FIG. 2, in accordance with some embodiments.

FIG. 2 illustrates coordinate frames in relation to sensors of system 10 that they may be associated with, in accordance with some embodiments. FIG. 3 illustrates the coordinate frames shown in FIG. 2 in a manner that may be used to explain the transformations between them, in accordance with some embodiments. For the mathematics of the transformations to work in these embodiments, the position and orientation of all of these coordinate frames should be derived, calculated, known, or input in some manner to the control system associated with system 10.

In embodiments of a multi-jointed robotic system, such as, for example, system 10, typically a reference coordinate frame called a world coordinate frame may be chosen and used as a common reference for the other coordinate frames of the system. The position and orientation of the other coordinate frames with respect to the reference coordinate frame may be derived, calculated, known, or input to the control system in various ways. In some cases, actual measurements may be manually or automatically taken to find the position and orientation of the coordinate frames with respect to the reference frame. Automatic measurements may be obtained by coupling sensors such as position sensors to the sensors associated with the coordinate flames. The coordinate frames whose position and orientation are known through manual or automatic measurements may be referred to as "measured" coordinate frames.

In some embodiments, the position and orientation of the coordinate frames are known by sensing these parameters by coupling sensors to one or more tracked objects that the coordinate frames are associated with. Various types of sensors such as electromagnetic position sensors or encoders may be used. For example, an electromagnetic sensing coil may be used to track its location and orientation in an established electromagnetic field created by another component of the system. In some embodiments, optical tracking may be used, wherein one or more cameras are used to track features on a tracked object, such as a light-emitting feature, a reflective feature such as a reflective ball, a distinctive surface, and/or the like. The cameras may be placed on the tracked objects or the tracked objects may include the reflective feature that is tracked by the cameras. In some embodiments, a sensor may comprise an encoder, wherein the encoder may provide orientation information (for example, an orientation of one degree of freedom). The measurements from these sensors may be given in relation to some other reference such as the reference coordinate frame or any another coordinate frame. The coordinate frames whose position and orientation are known through sensing may be referred to as "sensed" coordinate frames within this disclosure, it is recognized that the sensors or cameras may be placed in a variety of locations on the operator's body, the UID, the robotic tool, as well as other parts of the system.

In some embodiments, the position and orientation of a coordinate frame may be assigned certain values or may be assumed to be similar or identical to another coordinate frame, as further described below.

Returning to FIG. 3, the left side of the figure shows three coordinate frames generally associated with the operator, whereas the right side shows three coordinate frames generally associated with the robot. On the left side, three coordinate frames are shown, the Eye coordinate frame 160, the UID Base coordinate frame 150, and the UID coordinate frame 140.

The Eye coordinate frame 160 is associated with the operator: its orientation in relation to the operator may be fixed but configurable. As an example, in some embodiments, the Eye coordinate frame may be associated with the operator's eyes but set to an angle of 30° to the horizon. This may be due to the fact that during a medical procedure the operator, such as a surgeon, may be looking at the images displayed on a monitor, which may be set at an angle. The surgeon may thus have to look down or look up in order to view the monitor. The angle of the Eye coordinate frame may thus be set on the basis of the angle of the monitor.

Referring back to the discussion of the various coordinate frames, the Eye coordinate frame is an example where it is assumed to have a certain orientation. It is understood that in other embodiments, angles other than 30° may be used as well. For the purposes of the mathematics involved in the coordinate frame transformations, the Eye coordinate frame may define how the operator perceives objects that he or she sees in terms of the position and orientation of the object. In addition, in some other embodiments, coordinate frames other than an Eye coordinate frame may be associated with the operator.

In some embodiments, the Eye coordinate frame may be measured instead of assumed. For example, a 3D tracker may be used to measure a head frame of the operator and determine the Eye coordinate frame. In some embodiments, in order to maintain stable teleoperation, the Eye coordinate frame may be measured on a periodic basis by the 3D tracker, instead of being tracked in real time.

In some embodiments, the UID Base coordinate frame 150 may be associated with a physical sensor of system 10 called the UID base 65. The UID base 65 may be placed anywhere in the environment of system 10. The location and orientation of the UID Base coordinate frame may be known in relation to a fixed coordinate reference system such as a world coordinate reference system, by direct measurement. Thus, the UID Base coordinate frame is an example of a measured coordinate frame. The UID Base coordinate system may be used by system 10 as a reference to obtain the location and orientation of the groundless UIDs 50.

In some embodiments, the coordinate frame 140 may be associated with the groundless UID and moves around in concert with the movement of the groundless UID itself. As the groundless UID may have sensors, the position and orientation of the UID coordinate frame with respect to the UID base coordinate frame may be known due to direct sensing. The arrow 155 indicates that the UID coordinate frame 140 may be sensed in relation to the UID Base coordinate frame 150. The UID coordinate frame is an example of a sensed coordinate frame.

In some embodiments, the groundless UID 50 may move about in six degrees of freedom (DOF), three of which are translational DOFs and the other three are rotation DOD's.

Referring to the coordinate frame 140 in FIG. 3, the translational degrees of freedom may be about the X, Y and Z axes. By convention, the roll, pitch and yaw axes are aligned to the X, Y and Z axes respectively. Thus, the roll axis is coincident with the X-axis of the coordinate frame 140 by this convention. However, in other embodiments, other conventions may be followed such as the roll axis may be aligned to the Y axis. The concepts described in this disclosure equally apply for other embodiments as well. In this section, it will be assumed that the roll axis will be aligned to the X-axis. More embodiments associated with system 10 will be described below.

The coordinate frames generally associated with the robot are shown on the right side of FIG. 3. In some embodiments, a Camera coordinate frame 130 may be associated with the camera 45. Using the embodiment described above, the roll axis of the camera may be aligned with the X-axis of the Camera coordinate frame 130. As the operator sees the images obtained by the camera, in some embodiments it may be assumed that the Eye coordinate frame 160 and the Camera coordinate frame 130 are aligned. For example, in some embodiments, teleoperation is performed when the Eye coordinate frame matches the Camera coordinate frame, and the UID coordinate frame matches the Grasper coordinate frame. In some embodiments, the Eye coordinate frame is set or assumed to match the Camera coordinate frame. In some embodiments, the Grasper coordinate frame and the UID coordinate frame may be misaligned.

An Arm Base coordinate frame 110 may be associated with the arm, specifically the active arm, that holds the robotic tool. This coordinate frame may be placed anywhere along the arm. For example, in some embodiments, the Arm Base coordinate frame 100 may be located at the base or at the first joint of the active arm. The active arm may comprise of motors or actuators along with other components as opposed to the passive arm which may have only passive components. In some embodiments, the Arm Base coordinate frame is an example of a measured coordinate frame as its position and orientation in relation to a reference coordinate system may be also known due to direct measurements.

A Grasper coordinate frame 120 may be associated with the robotic tool. In some embodiments, similar to the UID coordinate frame 140 in relation to the UID, the Grasper coordinate frame 120 moves around in concert with the tool. Also similar to the UID coordinate frame, the Grasper coordinate frame 120 may be known in relation to the Arm Base coordinate frame 110 due to sensing. The active arm may have encoders on all its joints; these encoders provide the sensed values by which the Grasper coordinate frame 120 may be known in relation to the Arm Base coordinate frame 110. The arrow 115 indicates that the Grasper coordinate frame may be known in relation to the Arm Base coordinate frame, similar to how the UID coordinate frame 140 is sensed in relation to the UID Base coordinate frame 150.

In some embodiments, such as that illustrated in FIG. 2, the camera is seen to be held by a distinct passive arm/active arm combination. In other embodiments, the camera may be held by any of the robotic arms. In some embodiments, the camera coordinate frame may be known in relation to a coordinate frame at the base of the active arm holding it. However, as the position and location of all the active arms may be known in reference to the world coordinate system, in some embodiments it may not be necessary to call out or specify separately the coordinate frame associated with the active arm holding the camera. Thus, in this embodiment, the coordinate frame associated with the active arm holding the camera is not specified separately.

It is to be understood that throughout this disclosure the word "grasper" in the description and on the figures includes any type of robotic tool, such as, but not limited to, a grasper and a stapler. The words "robotic tool" and "grasper" are used synonymously. As specified earlier, although robotic tools generally include cameras as well, in this disclosure the camera and the Camera coordinate frame will be specified separately. There may be different methods of transforming the UID coordinate frame motion to the robotic tool or camera motion depending on the type of robotic tool or camera which is held by the arm. The arm in many embodiments is equipped with sensors to determine the type of robotic tool or camera mounted on it.

The objective of defining these coordinate frames for some embodiments is to transform the UID input to the output of the robotic tool. In other words, as the operator moves about the groundless UID, those movements are transformed to movements of the robotic tool in a way that can be comprehended by the operator. In some embodiments, in order to achieve this comprehension, the Eye coordinate frame and the Camera coordinate frame are assumed to be aligned so that as the operator manipulates the groundless UID, the motion of the robotic tool as seen by the camera and displayed on the monitor corresponds to the hand movements.

In some embodiments, the translational movements and pitch and yaw movements are generally more comprehendible than roll motions. Misalignments in the roll axes of the groundless UID and the robotic tool causes movements of the tool that may be hard to understand. For example, misalignments may cause the motion of the robotic tool to be more difficult to predict, or may cause the robotic tool to move in a way different from what is desired by the operator when performing a motion with the UID. This may lead to increased mental strain on the operator, which may cause the operator to slow down and which may be detrimental to the execution of a successful surgical procedure. In system using groundless UIDs that are free to move about in space, it may be a difficult to exactly align the UIDs to the robotic tools. Yet even in the scenario of system 10, transforming the roll motion of the groundless UID to roll motion of the grasper in a way that the operator can understand needs to be accomplished. Some concepts described in this disclosure accomplish this and will be explained in later sections. The method of how to transfer rotational displacement from the UID (master) to the robotic tool (slave) and the problem of misalignment during transfer of roll from master to slave is now described.

Transfer of Rotational Displacement

Figure 4:
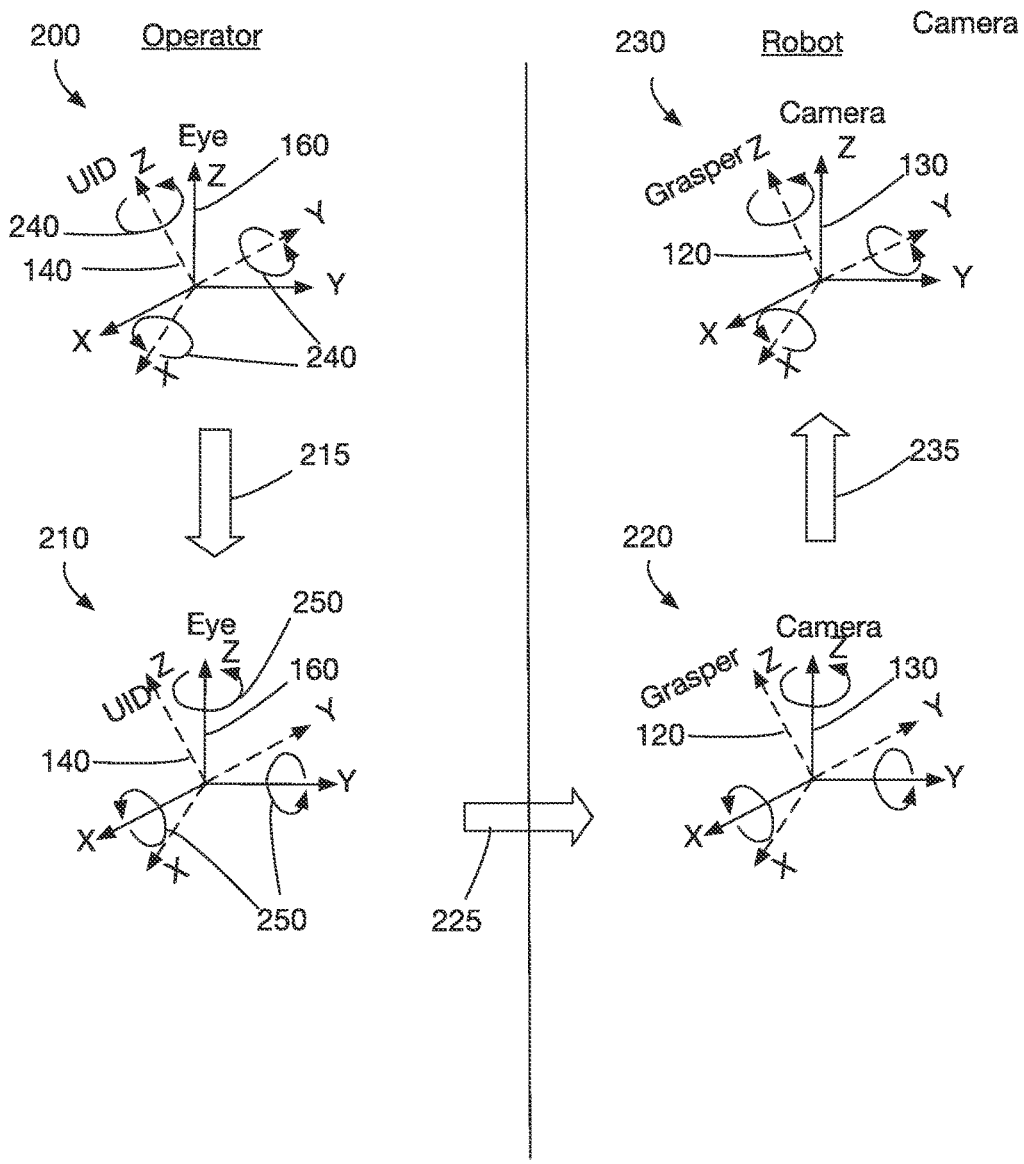
FIG. 4 illustrates a transfer of a movement when the grasper and groundless UID of a hyperdexterous surgical system are aligned, in accordance with some embodiments.

FIG. 4 illustrates how a rotation of the UID is transferred to the robotic tool, in accordance with some embodiments. As specified earlier, although robotic tools also generally include robotic cameras, for the purposes of coordinate transformations, the camera and the coordinate frame associated with the camera may be specified separately. For example, as illustrated in 200 in FIG. 4, the UID coordinate frame 140 and the Eye coordinate frame 160 are shown with the same origin. The arrows 240 illustrate that the groundless UID 50 has experienced a rotation motion that has a roll, pitch and yaw component. The operator has to ultimately comprehend this motion in his or her frame of reference (since he or she may very well be causing this motion), the Eye coordinate frame 160. Thus, the motion in the UID coordinate frame is converted into the Eye coordinate frame. Arrow 215 shows this transformation. To transform the rotation from the UID coordinate frame to the Eye coordinate frame, two transformations may occur. The first transformation is to transform the rotation from the UID coordinate frame to the UID Base coordinate frame. The second transformation is to transform the rotation from the UID base coordinate frame to the Eye coordinate frame.

In some embodiments, mathematically, the transformations of rotations may be done using rotation matrices. The convention followed in this embodiment to represent the rotation matrix is $_B^A R$ is the rotation matrix of coordinate frame A with respect to the coordinate frame B. In other words, in order to rotate a vector in coordinate frame A, it is multiplied by the rotation matrix to find its orientation in coordinate frame B. Thus the two transformations referred to above from the UID to UID Base and from the UID Base to the Eye coordinate frame may be expressed as one operation as:

$$_{EYE}^{UID}R = {_{EYE}^{UID\ Base}}R * {_{UID\ Base}^{UID}}R \qquad \text{Eqn. 1}$$

Recognizing that $_B^A R = {_B^A}T$ where T depicts the transpose operation, Eqn. 1 may be written as $$_{EYE}^{UID}R = {_{UID\ BaseE}}{^{EYE}R^{T}} * {_{UID\ Base}^{UID}}R \qquad \text{Eqn. 2}$$

Next, still referring to FIG. 4, the rotation of the UID with respect to the Eye coordinate frame is transferred over to the grasper with respect to the Camera coordinate frame and is shown by the arrow 225. The motion of the grasper with respect to the Camera coordinate frame is what is desired. Mathematically, the rotation of the grasper with respect to the Camera coordinate frame may be written as:

$$_{Camera}^{Grasper}R = {_{EYE}^{UID}}R \qquad \text{Eqn. 3}$$

The grasper, as shown in FIG. 2, is coupled to the active arm 70 that subsequently is coupled to the passive arm 75. It is mathematically convenient although not necessary to use a stationary frame of reference to track the grasper movements. In some embodiments, the base of the passive arm, referred to as the "Arm Base," provides such a convenient location to locate the stationary coordinate frame. It is to be noted that although this location is described as stationary, during initial set up of system 10 the passive arm may be located anywhere appropriate along the side of the bed. Hence, the movement of the grasper with respect to the Camera coordinate frame can be transformed into the movement of the grasper with respect to the Arm Base coordinate frame. This is shown by arrow 235 in FIG. 4 and is depicted mathematically as:

$$_{Arm\ Base}^{Grasper}R = {_{Camera}^{Arm\ Base}}R^{T} * {_{Camera}^{Grasper}}R \qquad \text{Eqn. 4}$$

Thus Eqns. 1 through 4 can be combined into one equation:

$$_{Arm\ Base}^{Grasper}R = {_{Camera}^{Arm\ Base}}R^{T} * {_{UID\ BaseE}^{EYE}}R^{T} * {_{UID\ Base}^{UID}}R \qquad \text{Eqn. 5}$$

This equation depicts an embodiment of the transformation of the UID motion with respect to IAD Base coordinate frame to the motion of the Grasper with respect to the Arm Base. The quantity $_{UID\ Base}^{UID}R$ forms the control input and is sensed; the UID orientation is sensed with respect to the UID Base. The quantity $_{Arm\ Base}^{Grasper}R$ forms the control output and is calculated as specified in Eqn. 5. The robotic tool may then be manipulated with respect to the Arm Base in accordance with the calculated value.

Effect of Misalignment of UID and Robotic Tool on Roll Motion

Figure 5:
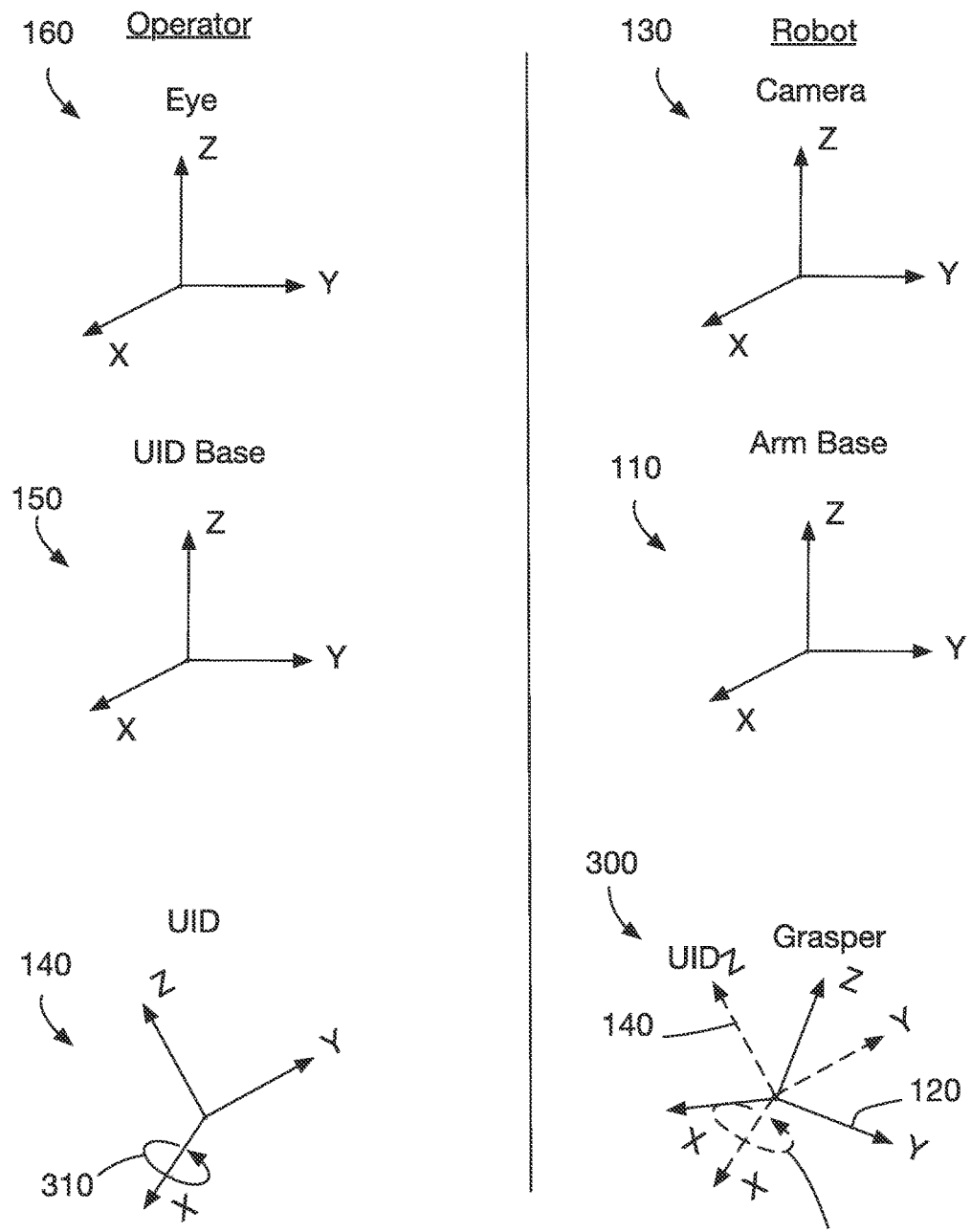
FIG. 5 illustrates a transfer of a roll movement when the grasper and groundless UID are not aligned in accordance with some embodiments.
Figure 6A:
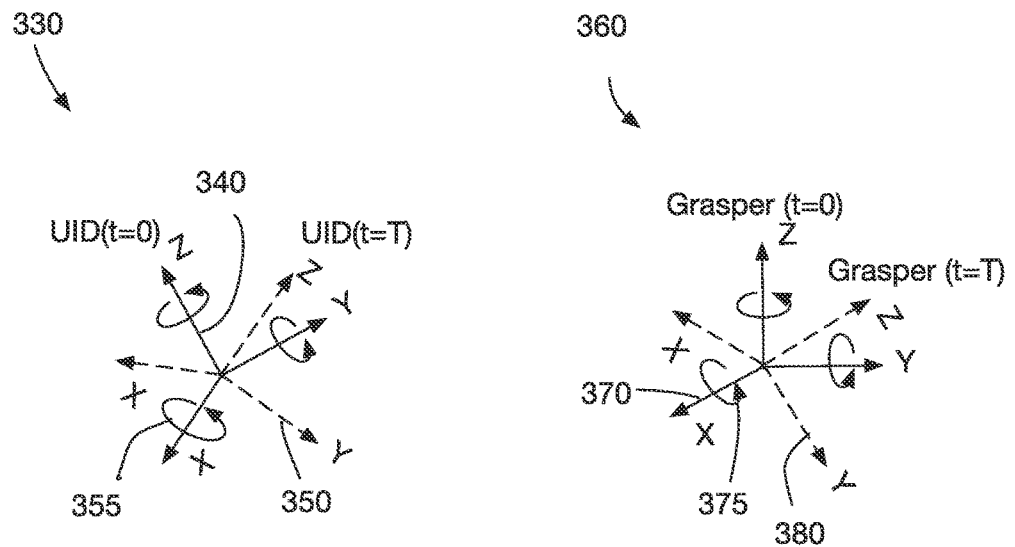
FIG. 6A illustrates coordinate frames in absolute control mode, in accordance with some embodiments.
Figure 6B:
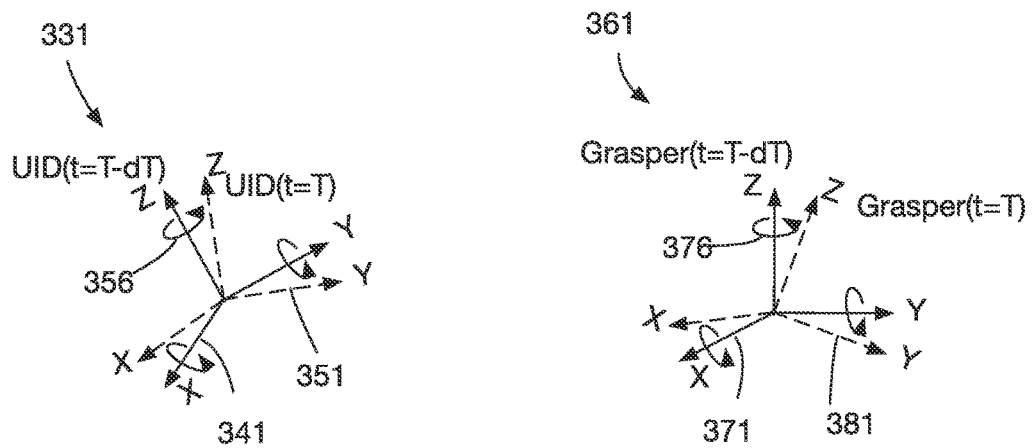
FIG. 6B illustrates coordinate frames in incremental control mode, in accordance with some embodiments.

If the groundless UID 50 and the robotic tool 40 are misaligned or when $_{EYE}^{UID}R = {_{Camera}^{Grasper}}R$, roll motion of the groundless UID may not be transformed in a comprehendible manner. FIG. 5 illustrates an example of a roll motion where the groundless UID and robotic tool are misaligned, in accordance with some embodiments. For the purposes of illustrating the effect of misalignment, the Eye coordinate frame 160, the UID Base coordinate frame 150, the Camera coordinate frame 130 and the Arm Base coordinate frame 110 may be considered aligned. Further, again for the purposes of this example, the UID coordinate frame 140 and Grasper coordinate frame 120 are not in rotational alignment as shown clearly in graph 300 where the two coordinate frames are overlaid on top of each other with their origins at the same location. The UID coordinate frame 140 is shown by dashed lines to distinguish it from the Grasper coordinate frame 120.

On graph 140, assuming that the UID roll, pitch, and yaw axes are respectively aligned with the X, Y, and Z Axes of the coordinate frame, if the UID experiences a roll motion, the motion may be depicted by arrow 310. Since as stated above all coordinate frames except the UID coordinate frame and Grasper coordinate frame are aligned, this roll motion of the UID when transferred to the robotic tool may occur along the dashed arrow 320 in graph 300, resulting in unwanted pitch and yaw motion. If the roll axis of the robotic tool is aligned along the X-axis of the Grasper coordinate frame 120, the robotic tool will rotate along the dashed path 320—in other words, the robotic tool may exhibit a wobbling motion. Further, the wobbling motion becomes more pronounced with larger misalignments. The motion of the robotic tool may be visualized as a cone originating at the origin of the coordinate frames. The robotic tool may thus undergo a motion that is not a roll motion. The operator may not fully understand why this type of motion occurs when all that was desired was a roll motion of the robotic tool. For completeness, it is to be stated that the X, Y, Z positions may not be affected by the misalignment and are applied as required to the robotic tool based on the UID motion. Thus in the concepts described below, various methods to preserve the roll motion when misalignment exists are described.

Control Modes

In some embodiments, the orientation of the robotic tool can be calculated by knowing how much the orientation has changed relative to an initial orientation. The initial orientation may be measured in various ways. For example, in a method called the "absolute control mode", the initial orientation is established when the user engages a drive (may also be referred to as a "clutch") associated with system 10. For reference, engaging the drive informs system 10 that the motion of the groundless UIDs needs to be translated into movements of the robotic tools. Further in a disengaged state, the robotic tools are held steady and are not affected by the motion of the groundless UID. In the absolute control mode, one embodiment of the rotation matrix of the robotic tool with respect to the Arm Base coordinate frame may be expressed as:

$$_{Arm\,Base}^{Grasper(i=t)}R = _{Camera}^{Arm\,Base}R \ast _{Eye}^{T} \ast _{Eye}^{UID(i=\tau)}R = _{Eye}^{UID(i=\tau)}R \ast _{Camera}^{T} \ast _{Camera}^{Grasper(i=0)}R \qquad \text{Eqn. 6}$$

where the superscripts t=0 or t=τ indicate that the coordinate frame that the superscript applies to is to be taken at time 0 or at time τ, noting that t=0 is established at the instant when driving action occurs and time τ is the current instant of time.

In Eqn. 6, the last two terms of the right hand side ($_{Eye}^{UID(i=0)}R^T \ast _{camera}^{Grasper(i=0)}R$) indicate the initial misalignment of the tool and the UID. This misalignment may remain throughout the drive period.

In some embodiments, in another method to calculate the orientation of the robotic tool, the initial orientation is taken to be the orientation in the immediately preceding sampling instant. This method may be called the "incremental control mode". Here the equations may be expressed as:

$$_{Arm\,Base}^{Grasper(i=\tau)}R = _{Camera}^{Arm\,Base}R \ast _{Eye}^{T} \ast _{Eye}^{UID(i=\tau)}\Delta R \ast _{Camera}^{Arm\,Base}R \ast _{Camera}^{Grasper(i=t-d\tau)}R \qquad \text{Eqn. 7}$$

where τ is the present instant in time, τ–dτ indicates the immediately previous instant in time, and where $_{Eye}^{UID(i=\tau)}\Delta R$ is given by:

$$_{Eye}^{UID(i=\tau)}\Delta R = _{Eye}^{UID(i=\tau)}R \ast _{Eye}^{UID(i=\tau-d\tau)}R^T \qquad \text{Eqn. 8}$$

Further, embodiments of the two rotation matrices on the right hand side of Eqn. 8 may be written as $$_{Eye}^{UID(i=\tau)}R = _{Eye}^{Arm\,Base}R \ast _{Arm\,Base}^{UID(i=\tau)}R \qquad \text{Eqn. 9}$$

and $$_{Eye}^{UID(i=\tau-d\tau)}R = _{Eye}^{Arm\,Base}R \ast _{Arm\,Base}^{UID(i=\tau-d\tau)}R \qquad \text{Eqn. 10}$$

Thus, Eqn. 6 allows the transformation of the rotational motion of the groundless UID to the rotational motion of the robotic tool using the absolute control mode. Eqn. 7 allows the transformation of the rotational motion of the groundless UID to the rotational motion of the robotic tool using the incremental control mode. These two control modes may be used to explain the concepts of allowing motion when the master and slave are misaligned. Systems using grounded UIDs typically use the absolute control model. However, the incremental control mode is a concept that was derived in relation to systems using groundless UIDs, such as system 10.

Euler Angles

Euler Angles are a set of three angles from which the rotation matrix may be derived. These three angles inform how an initial coordinate frame may be rotated to obtain a resultant coordinate frame. Euler angles follow from Euler's Rotation Theorem, which states that an arbitrary rotation may be described by only three parameters (called the Euler angles). A detailed description may be found in Craig, John J., *Introduction to Robotics: Mechanics and Control*, 1989, which is hereby incorporated by reference herein in its entirety and should be considered a part of this specification. However for the purposes of this disclosure, a rotation matrix can be characterized by the Euler angles. Based on this brief description, two functions are defined which will be used as described below, in accordance with some embodiments.

The first function $f_{EulerYPR}$ may be defined as:

$$(yaw, pitch, roll) = f_{EulerYPR}(R) \qquad \text{Eqn. 11}$$

and the second function $g_{EulerYPR}$ may be defined as:

$$(R) = g_{EulerYPR}(yaw, pitch, roll) \qquad \text{Eqn. 12}$$

In accordance with some embodiments, the function $f_{EulerYPR}$ takes a rotation matrix R as its input and outputs the three Euler angles yaw, pitch and roll. The function $g_{EulerYPR}$ takes the three Euler angles yaw, pitch and roll as its input and outputs a rotation matrix R. From this brief description, it may be stated that the Euler angles and the rotation matrix are synonymous mathematical definitions, resulting in the same rotation of a coordinate frame.

Movement—Wobble Suppression Method

As discussed earlier, it is advantageous in some embodiments to allow the robotic tool (the slave), such as a grasper, to be manipulated even if the groundless UID 50 (the master control) and the tool are not aligned. Again as stated earlier, the operator may be most sensitive to misalignments in the roll axis of the master and slave due to the effect illustrated in FIG. 5 where a roll motion of the groundless UID translates to a wobble or rotation along an undesired axis.

In some embodiments, selective alignment, such as along a roll axis, instead of full 3-axis alignment, may provide improved performance of the system. For example, an embodiment of the "wobble suppression" method may be used to allow the robotic tool to roll along its axis due to a roll motion of the groundless UID. In some embodiments, if the magnitude of the roll angle is larger than the magnitude of the pitch angle and the yaw angle of the groundless UID, only the roll motion is applied to the robotic tool. Movements in the pitch and yaw degrees of freedom may be ignored. Mathematically, this can be expressed as:
If:

$$|roll|>|pitch|+|yaw| \quad \text{Eqn. 13}$$

then, only apply the roll angle from the master to slave. In a more generic sense, if the roll angle satisfies some defined criteria in relation to a function of pitch and yaw, then system 10 may only apply the roll angle. For example, in some embodiments, it may be advantageous to only apply roll if the following condition is satisfied:

$$|roll| \pm k1*|pitch|+k2*|yaw| \quad \text{Eqn. 14}$$

where k1 and k2 may be coefficients found experimentally or set via user preference. In other embodiments, different ways of determining whether to only apply roll may be used. In addition, in some embodiments, pitch and yaw may be scaled or capped instead of ignored, subject to the satisfaction of one or more criteria.

Figure 7:
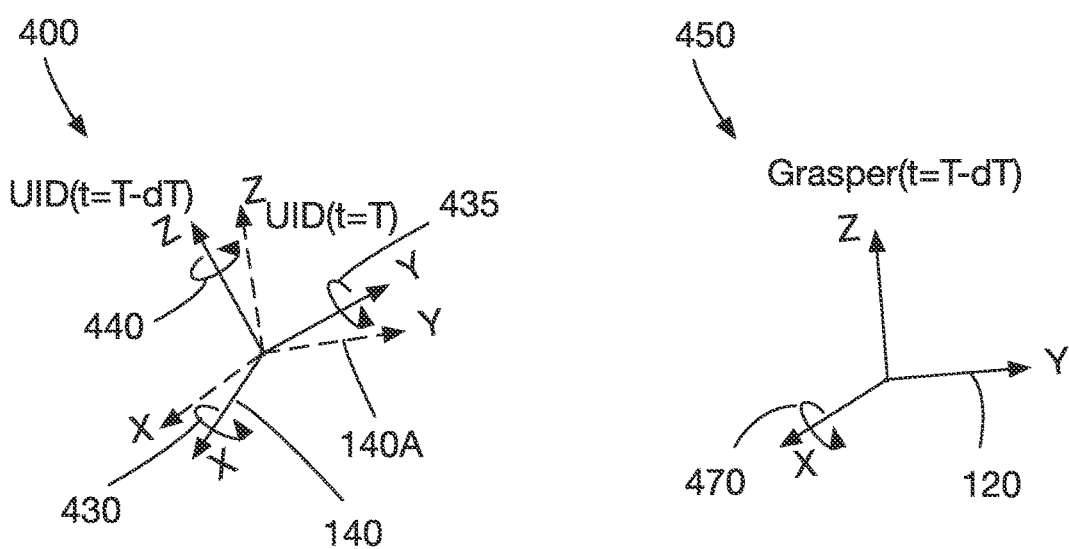
FIG. 7 illustrates a method to apply roll motion when master and slave controls are misaligned, in accordance with some embodiments.

FIG. 7 illustrates a "wobble suppression" method, in accordance with some embodiments. In graph 400, two UID coordinate frames 140 and 140A are shown. UID coordinate frame 140 occurs at time t=τ-dτ whereas UID coordinate frame 140A occurs at time t=τ. The enumeration 140 and 140A is chosen to emphasize that these two coordinate frames are associated with the same sensor, the UID—the difference between these coordinate frames is when they occur as explained just above. Arrows 430, 435 and 440 along the roll, pitch and yaw axes respectively indicate that the groundless UID 50 experienced motion on all three axes. Graph 450 indicates that the Grasper coordinate frame 120 is misaligned with respect to the UID coordinate frame at time t=T-dT. However, graph 450 also indicates that only one movement along the roll axis is applied to robotic tool. In the illustrated embodiment, Eqn. 13 was applied to determine that the magnitude of the roll angle of the groundless UID was larger than the sum of the magnitudes of the yaw and pitch angle, and hence only the roll angle was applied to the robotic tool. Hence at time t=T, in the graph 450, only the roll angle the groundless UID experiences is applied. Mathematically, if ΔR is as defined in Eqn. 8, then given that ΔR is known or can be calculated, the function $f_{EulerYPR}$ may be used to find the following angles:

$$(yaw_{UID}, pitch_{UID}, roll_{UID}) = f_{EulerYPR}(\Delta R) \quad \text{Eqn. 15}$$

The "wobble suppression" method then can be written as:

$$(\Delta R_{Grasper}) = g_{EulerYPR}(0, 0, roll_{UID}) \quad \text{Eqn. 16}$$

The advantage of using a "wobble suppression" method, in some embodiments, may be readily visualized by observing how humans roll an object such as a pencil between their thumb and forefinger. The human hand typically imparts motions in other degrees of freedom when rolling an object, while only intending to impart a pure roll motion. "Wobble suppression" offers a way to impart a pure roll motion to the robotic tool, for example, when a pure roll motion is intended but may not be achieved due to the mechanics of the hand. During the time system 10 is using Eqn. 13 to determine the motion of the robotic tool, if the operator wants to intentionally move in degrees of freedom other than along the roll axis, then a deliberate movement may be done in the desired direction so that Eqn. 13 is not satisfied. When Eqn. 13 is not satisfied, the motion along yaw and pitch axes may be transformed to the robotic tool. In other situations, wobble suppression may be used when the master and slave are misaligned.

Although in practice this method is robust, in some embodiments, fine pitch and yaw motions of the UID may be lost. This method also works best in the incremental control mode when the difference between the previous orientation and current orientation is small due to the small sampling instant Another method is now described which can work in the absolute control mode as well and preserve the pitch and yaw rotation of the UID.

Movement when Misaligned—Roll Projection

Figure 8:
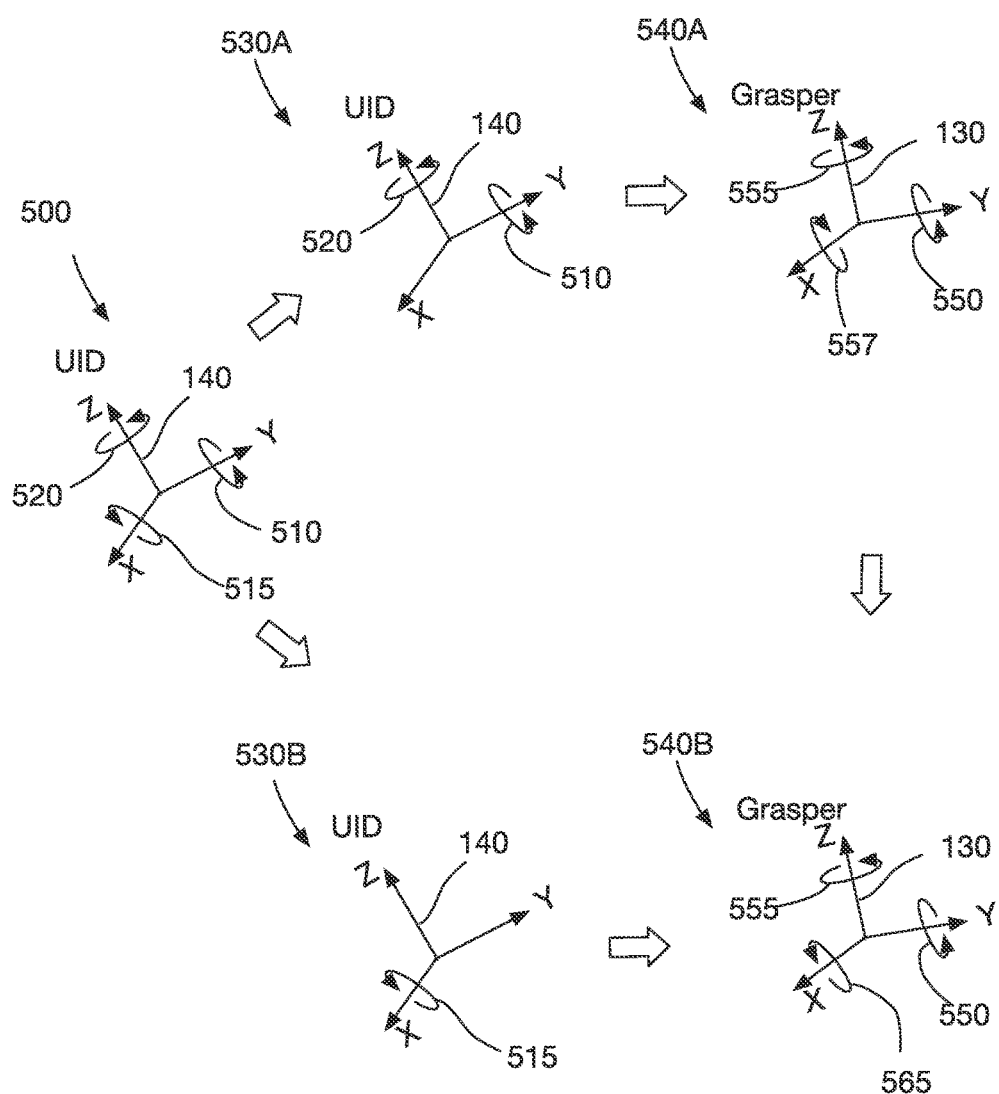
FIG. 8 illustrates another method to apply roll motion when master and slave controls are misaligned, in accordance with some embodiments.

FIG. 8 illustrates the application of a "roll projection" method, in accordance with some embodiments. In this figure, graph 500 illustrates that the UID may experience a motion in the UID coordinate frame 140 along the roll, pitch and yaw axes; the motion along these axes are designated by curved arrows 515 (roll), 510 (pitch) and 520 (yaw). In some embodiments, the UID motion (neglecting any translational motion) may be transformed to the Grasper coordinate frame in at least two separate but parallel steps.

In one step, the yaw and pitch motions are transformed. In the figure, this is indicated by graphs 530A and 540A. The transformed motion in the Grasper coordinate frame in graph 540A may have pitch (550), yaw (555) and roll (557) components despite the fact that the roll motion was suppressed when the transformation was taken.

In a second step, the roll angle of the robotic tool in the Grasper coordinate frame may be calculated by adding the roll angle of the UID to the roll angle obtained as a result of the step described above. This is indicated by graphs 530B and 540B. Thus, roll is handled independently of yaw and pitch. In some embodiments, Eqns. 6 and 7 are used for the transformation of the yaw and pitch from the UID coordinate frame to the yaw, pitch and roll of the Grasper coordinate frame. In some embodiments, this method may be advantageous as the wobbling motion caused by the misalignment of the groundless UID and robotic tool is eliminated. As an example, when the groundless UID only experiences a roll motion, misalignment causes unwanted pitch and yaw motion which is the cause of the wobble; which may be eliminated through the use of this method. Further, this method works in either the incremental or absolute control mode. Referring to FIG. 8, the rotation indicated by 510 and 520 in graph 530A is transformed into the rotation 550 (pitch), 555 (yaw) and roll (557) in the Grasper coordinate frame 130 of graph 540A. Roll angle 557 is summed with the roll angle 515 resulting in the final roll angle 565. The transformed yaw and pitch is then combined with the summed roll angle to compute the final motion of the robotic tool. Thus, in this method the pitch and the yaw motion are preserved. In addition, as stated above, this method works for the absolute and the incremental control mode. The equations below explain this method mathematically in steps, in accordance with some embodiments.

Step 1: Find the Euler angles for the UID $$(yaw_{UID}, pitch_{UID}, roll_{UID}) = f_{EulerYPR}(\Delta R_{UID}) \quad \text{Eqn. 17}$$

Since this method can work for either the incremental or absolute control modes, $\Delta R$ can be calculated for either mode. For the incremental mode $\Delta R$ is as defined in Eqn. 8. For the absolute control mode, the same equation can be used $d\tau$ made equal to 0, the instant when the drive is engaged.

Step 2: Calculate a new $\Delta R$ with $\text{roll}_{UID}$ set equal to 0

$$(\Delta R_{UID}) = g_{EulerYPR}(\text{yaw}_{UID}, \text{pitch}_{UID}, 0) \quad \text{Eqn. 18}$$

Step 3: Transform $\Delta R_{UID}$ to $\Delta R_{Grasper}$ $$(\Delta R_{Grasper}) = {}_{Camera}^{Arm\ Base}R^T * \Delta R_{UID} * {}_{Camera}^{Arm\ Base}R \quad \text{Eqn. 19}$$

Step 4: Find the Euler angles for the grasper $$(\text{yaw}_{Grasper}, \text{pitch}_{Grasper}, \text{roll}_{Grasper}) = f_{EulerYPR}(\Delta R_{Grasper}) \quad \text{Eqn. 20}$$

Step 5: Re-compute $\Delta$Re-compute $\Delta R_{Grasper}$ with roll angle calculated directly by adding the roll angle of the robotic tool as calculated from Eqn. 20 and the roll angle of the UID.

$$(\Delta R_{Grasper}) = g_{EulerYPR}(\text{yaw}_{Grasper}, \text{pitch}_{Grasper}, \text{roll}_{UID} + \text{roll}_{Grasper}) \quad \text{Eqn. 21}$$

As can be seen in Eqn. 21, the final $\Delta R$ may be calculated based on the transformed motion in the case of pitch and yaw and a roll angle calculated by adding the direct roll angle of the UID to the roll angle obtained while transforming pitch and yaw. This method would work most advantageously if the misalignment is less than +/-30 deg, although other angles are not excluded.

In general, either of the two methods ("wobble suppression" and "roll projection") can be used in accordance some embodiments to preserve the roll motion of the UID and apply the motion to the robotic tool, even if the master and slave controls are misaligned. Other advantageous concepts are now discussed in relation to system 10.

Applying Hierarchy, Decoupling and Scaling of UID Motions

In some embodiments, the motion of the groundless UID can be processed in a decoupled manner internally to system 10. In computing the final output of the robotic tool, input motion in each DOF may be analyzed and treated differently. For example, some input motions may be given precedence over other input motions—a system of hierarchy may be applied to compute the final output motion. In other words, while the operator moves the groundless UID in complex ways, internal to system 10, these motions may be decoupled and manipulated differently according to some established criteria.

As an example, if the operator rolls the groundless UID to perform an action such as applying a suture to tissue, there may be a natural tendency for the wrist to apply a translational motion simply due to the mechanics of how the human wrist works. In such cases, if certain criteria are met, the translational components may be suppressed or removed while transforming the UID movements to the robotic tool.

Figure 9A:
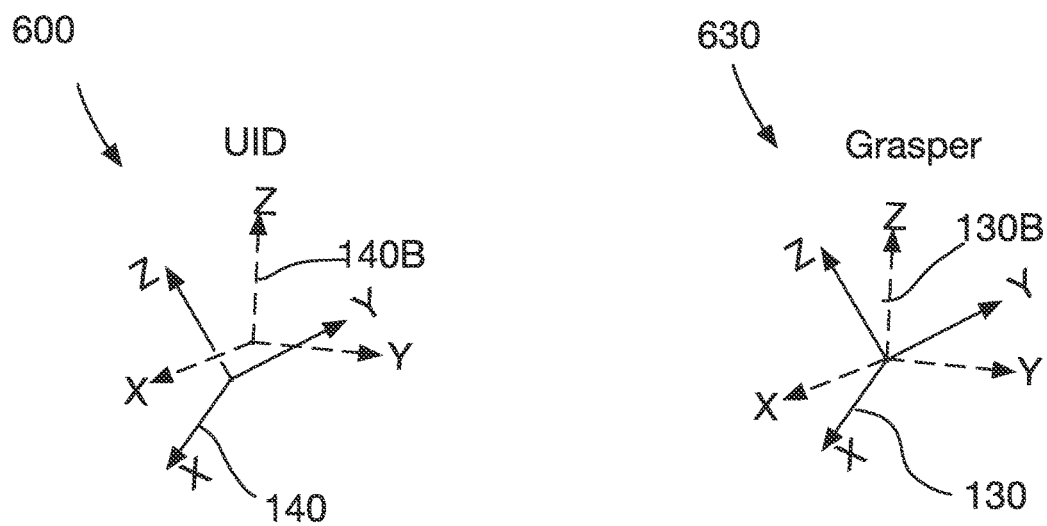
FIG. 9A illustrates a decoupling and scaling operation, in accordance with some embodiments.

For example, FIG. 9A illustrates decoupling and scaling translational components when transforming UID movements to the robotic tool, in accordance with some embodiments. In this figure, graph 600 depicts that the UID experiences a motion from an initial position shown by the UID coordinate frame 140 to a position shown by the coordinate frame 140B (shown by dashed lines). It can be seen from the figure that the motion involved both a rotation and a translation. Although not obvious from the figure, the rotation may occur along one or multiple of the roll, pitch and yaw axes.

As shown in FIG. 9A, graph 630 illustrates the motion of the robotic tool. Here the initial position of the robotic tool is shown as 130. In accordance with the illustrated embodiment, the new position of the robotic tool corresponding to the UID coordinate frame 140B is shown by the coordinate frame 130B (by dashed lines). The translation motion of the UID shown in graph 600 has been removed from the transformed motion of robotic tool as shown by graph 630. Although in this example, the translation motion has been removed, in other concepts the translation motion may be scaled. For example, the scaling factor may be 0.5; this would result in the new position of the robotic tool being translated only half as much as the translation the UID experienced.

Figure 9B:
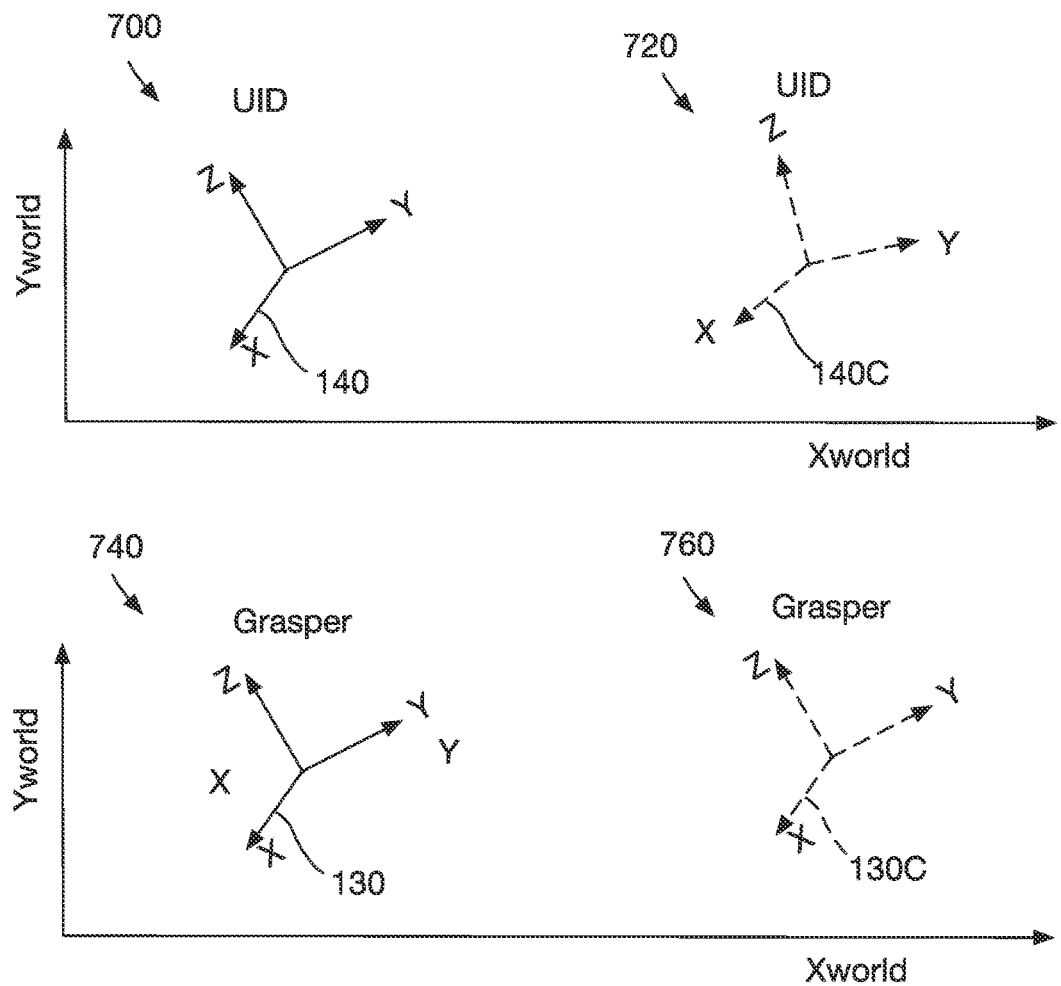
FIG. 9B illustrates another example of a decoupling and scaling operation, in accordance with some embodiments.

FIG. 9B illustrates another example of decoupling and scaling, in accordance with some embodiments. Here graphs 700 and 720 refer to the initial and final position of the groundless UID respectively and graphs 740 and 760 refer to the initial and final position of the robotic tool respectively. For the sake of clarity, the graphs 700 and 720 are assumed to occur in the XY plane of a world coordinate system to indicate that the UID coordinate frame has been translated and rotated from its initial position in 700 to its final position in 720. The translation is seen to be relatively large compared to the rotation. In graphs 740 and 760, the initial and final positions of the robotic tool are shown. For the sake of clarity, these graphs are also shown in the same world coordinate system. In the illustrated embodiment, only the translation motion has been preserved and transformed between the UID and the robotic tool and the rotation has been removed. Thus, FIGS. 9A and 9B illustrate examples of the concept of decoupling and scaling motion of the groundless UID while transferring that motion to the robotic tool.

In some embodiments, the above examples may be generalized and expressed mathematically as below.

If the total motion of the groundless UID is represented by ${}_{Eye}^{UID}T$ then:

$$ {}_{EYE}^{UID}T = \begin{bmatrix} {}_{EYE}^{UID}R & {}_{EYE}^{UID}P \\ 0 & 1 \end{bmatrix} \quad \text{Eqn. 22}$$

where ${}_{Eye}^{UID}R$ is the rotation matrix of the UID coordinate frame with respect to the Eye coordinate frame and ${}_{Eye}^{UID}P$ is the position vector representing the translation of the groundless UID with respect to the Eye coordinate frame. If R is a 3×3 rotation matrix and P is a 3×1 translation matrix then the last row of T is a 1×4 matrix where the 0 in Eqn. 22 is a short form notation for [0 0 0].

Similarly, if the total motion of the robotic tool is represented by ${}_{Arm\ Base}^{Grasper}T$, then:

$$ {}_{Arm\ base}^{Grasper}T = \begin{bmatrix} {}_{Arm\ Base}^{Grasper}R & {}_{Arm\ Base}^{Grasper}P \\ 0 & 1 \end{bmatrix} \quad \text{Eqn. 23}$$

where ${}_{Arm\ Base}^{Grasper}R$ is the rotation matrix of the Grasper coordinate frame with respect to the Arm Base coordinate frame and ${}_{Arm\ Base}^{Grasper}P$ is the ion vector representing the translation of the grasper with respect to the Arm Base coordinate frame. It is to be recognized that $_{Arm\ Base}{}^{Grasper}T$, $_{Arm\ Base}{}^{Grasper}R$ and $_{Arm\ Base}{}^{Grasper}P$ are transforms of $_{Eye}{}^{UID}T$, $_{Eye}{}^{UID}R$, and $_{Eye}{}^{UID}P$. In some embodiments, the last row of the right hand side of Eqn. 23 may be interpreted in the same manner as the last row of the right hand side of Eqn. 22 as described above.

Now, in accordance with some embodiments, the final applied motion of the robotic tool may be written as some general function φ of the transformed matrices $_{Arm\ Base}{}^{Grasper}R$ and $_{Arm\ Base}{}^{Grasper}P$ as:

$_{Arm\ Base}{}^{Grasper}M_{Final} = \varphi(_{Arm\ Base}{}^{Grasper}R, _{Arm\ Base}{}^{Grasper}P)$  Eqn. 24A For example, as illustrated in FIG. 9A, $_{Arm\ Base}{}^{Grasper}P$ is set to 0. In some embodiments, the system may check to see if the magnitude $|_{Arm\ Base}{}^{Grasper}P|$ is less than a threshold value. The threshold value may be set by the user or automatically or semi-automatically determined by the system or just pre-programmed in the system. In some embodiments, the value of $_{Arm\ Base}{}^{Grasper}P$ may be scaled instead of being set to 0. Any other appropriate value, such as, but not limited to $0.5 *_{Arm\ Base}{}^{Grasper}P$ may be used.

Similarly, in the example of FIG. 9B, $_{Arm\ Base}{}^{Grasper}R$ may be set to I (the identity matrix). In this case the system 10 may check to see if the magnitude $|_{Arm\ Base}{}^{Grasper}P|$ is larger than a threshold value. Again, the threshold value may be set by the user or be automatically or semi-automatically determined by the system or just pre-programmed in the system. In addition as above, in some embodiments it is also not necessary for the value of $_{Arm\ Base}{}^{Grasper}R$ to be set to I. Any other appropriate scaling factor may be used. To apply the scaling, the component yaw, pitch and roll angles may be first found using Eqn. 17, These angles may then be scaled and the new rotation matrix may be found using Eqn. 18.

In some embodiments, the hierarchical transformations may be configured such that rolling motions are easier to make followed by pitch and yaw motions, followed by translation motions. For example, to configure this behavior, Eqn. 24A along with Eqn. 11 and 12 may be used as below. The final applied motion may be written as:

$_{Arm\ Base}{}^{Grasper}M_{Final} = \varphi(_{Arm\ Base}{}^{Grasper}R2\delta *_{Arm\ Base}{}^{Grasper}P)$  Eqn. 24B Where (yaw,pitch,roll) = $f_{EulerYPR}(_{Arm\ Base}{}^{Grasper}R)$  Eqn. 24C And where the yaw, pitch and roll may be calculated from:

(yaw,pitch,roll) = $f_{EulerYPR}(_{Arm\ Base}{}^{Grasper}R)$  Eqn. 24D

In some embodiments, the coefficients α, β, γ, δ, may be adjusted by the user or preset by the robotic system during set up or adjusted in other ways. They may also be adjusted based on the value of the translation or the yaw, pitch and roll angles, For example, in one configuration, the coefficients tray be set as below:

(α,β,γ,δ) = (0.5,0.5,1,0.25)  Eqn. 24E

This configuration may make the roll motion easier to achieve compared to pitch and roll (with coefficients of 0.5) which in turn may be easier to achieve than translation (with coefficient of 0.25). In other words, the translation motion is suppressed most followed by the pitch and yaw. The roll motion is not suppressed at all, In some embodiments, the coefficients may be based on other properties of the motion rather than just the magnitude. For example, the coefficients may be adjusted based on speed, acceleration or other appropriate properties. As one example, if the speed of translation is slow, then δ may be set to a low or zero value in Eqn. 24E. This would have the effect that if the speed of translation of the groundless UID were slow, the translation motion would be suppressed when calculating the final output of the tool. Similarly, in some embodiments, if the angular velocity with which the user applies a roll motion to the groundless UID were high or higher than some preset or user settable value, then the coefficients α,β associated with the yaw and pitch DOFs may be set to a zero or low value. This would have the effect of suppressing the yaw and pitch motion made by the user as he or she rolled the groundless UID at some high rate (higher than some threshold value which may be set by the user or set by the system). Thus, it may be seen that the coefficients may be set on physical properties such as velocity. Other properties such as acceleration may also be used.

Thus, in some embodiments, the motion of the UID can be treated in a decoupled manner and the system 10 may decide how much of each decoupled components may be applied to the final motion of the robotic tool based on some established criteria. In addition, by adjusting the coefficients, each component of the motion may be emphasized or deemphasized to achieve different behaviors.

Anisotropic Scaling

Figure 10:
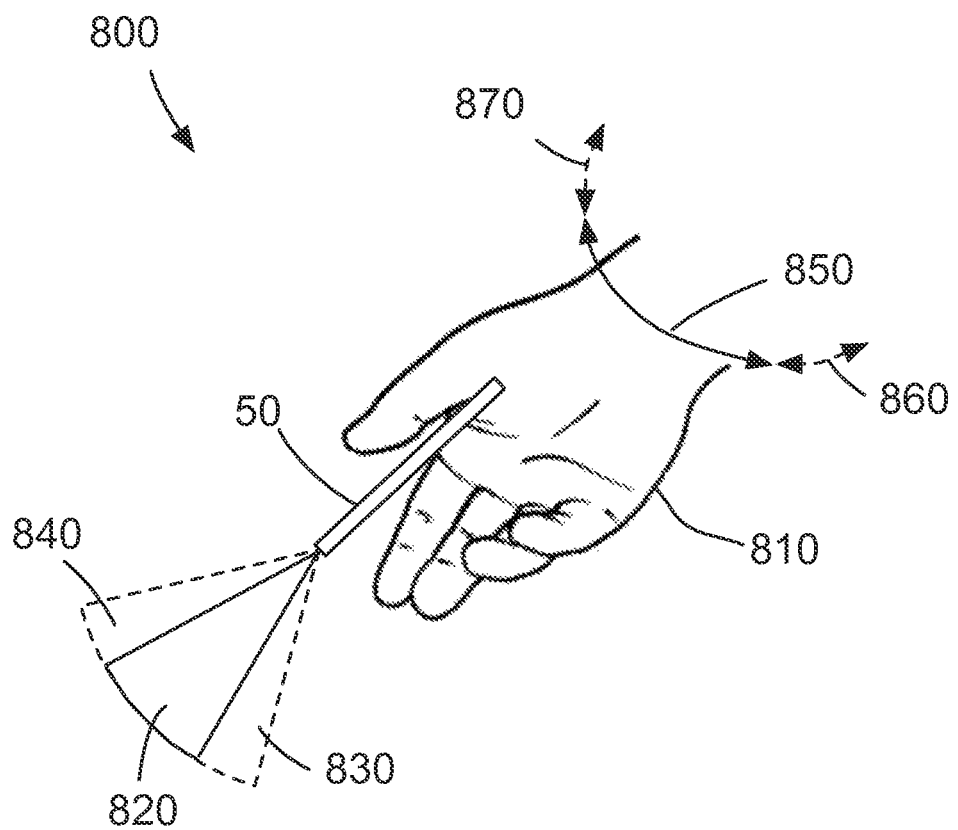
FIG. 10 illustrates anisotropic scaling, in accordance with some embodiments.

FIG. 10 illustrates an example of anisotropic scaling, in accordance with some embodiments. In some embodiments, the motion may be scaled differently depending on various conditions. For example, FIG. 10 shows a human hand 810 of an operator 20 holding a groundless UID 50. The curved arrow 850 indicates a comfortable range of motion of the hand due to wrist motion. Curved arrows 860 and 870 drawn with dashed lines illustrate regions where the wrist can extend to but is strained. The operator may feel discomfort while trying to access these regions. In the illustrated embodiment, the cone 820 extending axially from the groundless UID represents the region that can be accessed while moving the wrist along the curved arrow 850 while the cones 830 and 840 illustrated by dashed lines represent regions that may be accessed by moving the wrist along curved arrows 860 and 870. In some embodiments, to make the operation of the system 10 easier, the motion of the UID may be scaled differently when it is transformed into the motion of the robotic tool, depending on whether the operator's wrist is located along curved arrow 850 or along 860 or 870.

For example, in a particular embodiment, if the wrist is located along curved arrow 850 corresponding to cone 820, the scaling of the motion between the UID motion and robotic tool may be 1:1. On the other hand, if the wrist is located along 860 and 870 corresponding to regions 830 and 840, the scaling of the motion between the UID motion and robotic tool may instead be 2:1. This means that the rotations angles (roll, pitch and yaw) if operating along the curved arrows 860 and 870 may be doubled. With this type or arrangement, in the regions where the wrist may be strained, the system amplifies the motions of the wrist in an effort to reduce the difficulty in operating in such regions.

If considering only rotation, the mathematical description of anisotropic scaling in some embodiments may be given below. If $\Delta R_{Grasper}$ corresponds to the rotation matrix corresponding to the rotation of the UID then the Euler angles $yaw_{Grasper}, pitch_{Grasper}, roll_{Grasper}$ may be found using Eqn. 20. The final applied rotation may then be written as $(\Delta R_{Grasper\_final}) = g_{EulerYPR}$
$(\alpha * yaw_{Grasper}, \gamma * pitch_{Grasper}, \gamma * roll_{Grasper})$  Eqn. 25

In some embodiments, if the wrist is located along curved arrow 850, then α, β, γ may all be set to 1. On the other hand, if the wrist is along curved arrow 860 and 870, α, β, γ may all be set to a different value, for example 2.0. In addition, in some embodiments, α, γ, γ do not need to be set the same. They may be set to different values. Further, they may also be set differently in each region. For example, in region 860 these values may be set to 1.5, while in region 870 these values may be set to 2.0. In some embodiments, groundless UID 50 may be associated with different regions having different scaling values. Even though there may be two regions, for example, with one easy to reach and the other hard to reach, there may be more than two regions.

Figure 11A:
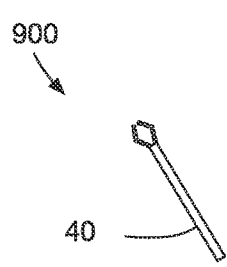
FIGS. 11A and 11B illustrate drivability cones, in accordance with some embodiments.
Figure 11B:
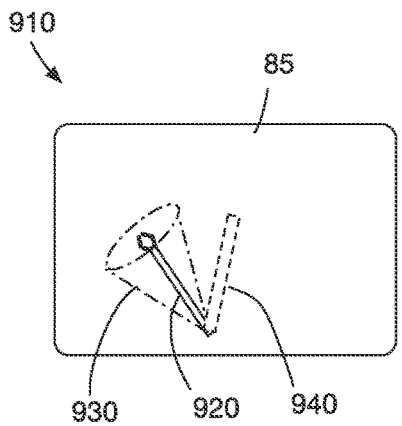
Figure 11C:
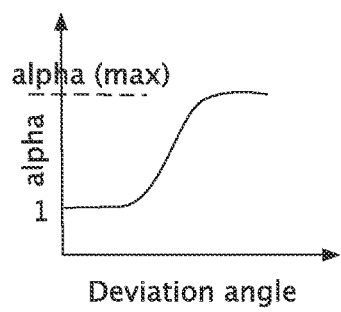
FIG. 11C illustrates a plot showing orientation angles as a function of a deviation angle, in accordance with some embodiments.

In FIG. 11A, a robotic tool 40 is illustrated, and in FIG. 11B, a screen 85 is illustrated showing the image of the robotic tool as seen by a robotic camera. FIG. 11C illustrates an example of how α, γ, γ may be set as a function of deviation from a comfortable position of the hand, in accordance with some embodiments. As the deviation angle increases beyond the comfortable position (indicated by the first bend in the curve) these parameters may be set differently until a maximum value is reached. As noted, α, β may not necessarily have the same values. In addition, γ may be set to 1 or may be set according to the methods discussed above.

In some embodiments, the concept of anisotropic scaling is not limited only to rotation. For example, the concept may be generalized using the form of Eqn. 24 as below:

$$_{Arm\ Base}^{Grasper}M_{Final} = \varphi$$
$$(\alpha*yaw_{Grasper}\beta*pitch_{Grasper}\gamma*roll_{grasper}\delta*$$
$$X_{Grasper}\epsilon*Y_{Grasper}*\mu*Z_{Grasper}) \quad \text{Eqn. 26}$$

where each coefficient, α, γ, γ, δ, ε, μ may be set to different values according to the location and orientation of the groundless UID or the location and orientation of the robotic tool, with $X_{Grasper}$, $Y_{Grasper}$, $Z_{Grasper}$ being the X, Y and Z components of the translation vector.

Anisotropic Scaling as Joint Limits

In some embodiments, the general equation for anisotropic scaling (Eqn. 26) may be used in various ways. In one example, when the operator drives the UID such that the one or more joints of system 10 may be nearing the their limits of operation, the scaling in Eqn. 26 may be modified automatically by system 10 such that the user finds it hard to go further into the region which would result in reaching the joint limits. For example, each joint may be associated with one or more regions based at least in part upon a position of the joint relative to its limit of operation, wherein the scaling in reach region may be different. In some embodiments, system 10 may scale the motion in the other axes in such a way that it prompts the user to move the UID and subsequently the joint nearing its limit, in a direction that prevents the joint or joints from reaching their limits.

In some embodiments, a display (for example, display 85) may be used to display joint limits in order to warn the user that one or more joints of system 10 are nearing their limits of operation, and to help guide the user in manipulating the UID such that the joint limit is not reached. For example, when one or more joints of system 10 are within a certain threshold from their limits of operation, a visual indication may be provided on the display, informing the user of the condition, and prompting them to adjust their manipulation of the UID in a direction that will avoid the joints reaching their limits. In some embodiments, other types of indications, such as audio indications, may be provided.

General Motion when Misaligned—Drivability and Ghost Images

Although techniques to preserve the roll motion of the UID are described above when the UID and robotic tool are misaligned, in some embodiments, the system 10 allows the robotic tool to follow the groundless UID when the misalignment is within a certain threshold. FIG. 11A and B illustrate examples where the robotic tool may follow the groundless UID based upon an amount of misalignment, in accordance with some embodiments.

In FIG. 11A, a robotic tool 40 is illustrated. In the illustrated embodiment, if an imaginary cone were to be drawn around the robotic tool and also imagining that the robotic tool and the groundless UID had the same origin, if the UID were within this cone, system 10 may allow the tool to follow the UID. In some embodiments, the imaginary cone is drawn about the roll axis of the robotic tool. The roll axis of the robotic tool with respect to the camera may be compared with a roll axis of the groundless UID with respect to the operator's eye.

In FIG. 11B, a screen 85 is illustrated showing the image of the robotic tool as seen by a robotic camera. As illustrated in the figure, dashed lines illustrate the imaginary cone. In addition, the groundless UID 50 is also rendered into the image. In some embodiments, the rendered image may comprise a 3-D object, model, or representation of the groundless UID 50. A composite image composed of what the camera sees and the rendered image of the robotic tool is displayed on the screen. The actual method of display such as if dashed lines are used or not is not material to this discussion. For reference, the rendered image of the robotic tool is called a "ghost image" and the imaginary cone around the robotic tool may be called the "drivability cone". In some embodiments, the "ghost image" of the robotic tool and/or the imaginary cone may be translucent for easier viewing. In some embodiments, the use of 3-D ghost image overlays allows the operator to better see discrepancies between the orientation of the UID and the orientation of the gripper or robotic tool. In some embodiment, an imaginary cone may be rendered around the groundless UID (or the "ghost image" or the groundless UID) in addition to or instead of around the robotic tool.

In some embodiments, the location of the rendering of the groundless UID on the screen may be chosen in the following manner. After the operator engages the drive to signify that he or she is ready to have the robotic tool follow the groundless UID, system 10 may map the location of the groundless UID to the origin of the Grasper coordinate frame. The orientation of the groundless UID and the robotic tool may or may not match system 10 can determine this as the two coordinate frames may ultimately be compared to the same reference coordinate system called the world coordinate frame. Regardless of orientation, the rendering of the groundless UID can be placed coincident with the origin of the Grasper coordinate frame as shown in FIG. 11B. For example, it can be seen from the figure that that the robotic tool and the groundless UID are misaligned but have the same origin. If the image of the groundless UID appears within this cone, then system 10 may allow the robotic tool to follow the groundless UID even if the two are not exactly aligned. The image of the groundless UID appearing within the cone signifies that the operator's perceived orientation of the groundless and robotic tool as presented to the operator on the live video feed on the screen are somewhat aligned. In some embodiments, the groundless UID with regards to an eye frame of the operator may be somewhat aligned with the robotic tool with regards to a camera frame used to present a view of the robotic tool to the operator. In other embodiments, the groundless UID and robotic tool may be somewhat aligned in reality (for example, compared to a world coordinate system). The angle of the cone may be set by the operator or determined through experience and set as an editable or a non-editable parameter within system 10. When the groundless UID is made to go outside this cone, system 10 may choose to not have the robotic tool follow the groundless UID. When this situation occurs, the robotic tool must be re-engaged before it can follow the groundless UID.

As described above, system 10 may in some embodiments not allow the robotic tool to follow the groundless UID when it is outside the drivability cone. In some embodiments, in order to re-engage the robotic tool, the user may manipulate the groundless UID so that it comes back inside the cone. In some embodiments, system 10 may be continually calculating the vector difference or the error between the orientations of the coordinate frames of the groundless UID and the robotic tool. As the operator brings the orientation of the groundless UID closer and closer to the orientation of the robotic tool, the error becomes smaller and smaller. If the operator continues to align the groundless UID, he or she may eventually overshoot the position and the error grows larger. At this instant, system 10 may command the robotic tool to follow the groundless UID. This method then allows the tool and the UID to be closely aligned. Control of the tool is allowed in this region.

In some embodiments, the cone may be of different sizes depending on the robotic tool being manipulated. For example, if a grasper or a stapler is being manipulated, the angle of the cone may be small, signifying lower tolerance for misalignment. On the other hand, if a robotic camera is being manipulated, the angle of the cone may be larger as more misalignment may be acceptable and tolerated. In some embodiments, shapes other than cones may be used.

In some embodiments, system 10 may have multiple controls schemes corresponding to different alignments between the groundless UID and the robotic tool. For example, the system 10 may use the schemes disclosed above, and/or the system may use different schemes depending on the alignment between the UID and the robotic tool. How motions of groundless UID are translated to the robotic tool may be different for each control scheme. For example, system 10 may allow for a control scheme when the groundless UID is substantially perpendicular with the robotic tool (for example, the roll axis of the robotic tool is perpendicular to the roll axis of the groundless UID). In some embodiments, the groundless UID being oriented 180 degrees relative to the robotic tool may also be associated with a control scheme. These different alignments may be thought of as multiple regions or cones with varying orientations with respect to the cone depicted in FIG. 11B. The transformation of the different degrees of freedom (for example, roll, pitch, and yaw) of the groundless UID into the motion of the robotic tool may be different for each of the different alignment regions. For example, in the region represented by a cone with axis perpendicular to the tool shaft and/or jaws of the tool, a pure pitch motion of the groundless UID may be mapped to a pure roll motion of the robotic tool.

In some embodiments, if the groundless UID becomes misaligned to a first alignment region of an object, such as a robotic tool, that corresponds to a first control scheme (for example, if the operator disengages the drive of the input system, causing the robotic tool to no longer follow the UID, and moves the UID to a different orientation before resuming control), the operator may be notified that the groundless UID is within a second alignment region associated with a second control scheme that is different than the first control scheme. In some embodiments, a drivability cone may be associated with each of different possible alignments, wherein the drivability cone for a particular alignment indicates an amount of misalignment that can be tolerated for the groundless UID to still control the robotic tool using the control scheme associated with that alignment. In some embodiments, the drivability cones for a particular alignment may be displayed on screen 85 as the ghost image of the UID approaches that alignment. These multiple alignment regions enable the operator to use the system in more flexible ways. For example, a robotic tool displayed on the left side of the screen 85 may be controlled by a UID in the operator's right hand by utilizing the 180-degree offset alignment region. By providing control schemes which allow for "misalignment" between the UID and the robotic tool, the system enables the operator to continue to efficiently use the robotic tools even when he or she is in a non-optimal orientation or position with respect to the display of the live video feed of the robotic tools, or with respect to the physical robotic tools themselves. This condition can occur frequently if the operator is positioned near the surgical bed, for example in order to operate manual or laparoscopic tools.

In general, these embodiments, which stem from the concept that the system may be driven even if the master and slave controls are misaligned by some limited amount, may improve the ease of use of system, especially one that may be controlled with groundless UIDs.

Minimized Error Driving Schemes

In some embodiments, the speed of the gripper may be adjustable depending on the vector error between the groundless UID and the robotic tool as long as the robotic tool is within the drivability cone. The speed may be adjusted based on some established criterion. For example, if the vector error is seen to increase, then the gripper may be sped up so that gripper catches up to the groundless UID. On the other hand, if the error is seen to decrease, then the gripper may be slowed down so that the UID catches up to the gripper. The error may be calculated in several ways. For example, in some embodiments, the angle between the X axis of the UID coordinate frame and the Grasper coordinate is found, why may be described mathematically below.

If as above R denotes the rotation matrix, then $$X_{UID} = {}_{Eye}^{UID}R(i,1) \qquad \text{Eqn. 27}$$

where ${}_{Eye}^{UID}R(i,1)$ is the first column of the rotation matrix of the UID coordinate frame with respect to the Eye coordinate frame.

Similarly $$X_{Grasper} = {}_{Camera}^{Grasper}R(i,1) \qquad \text{Eqn. 28}$$

where ${}_{Camera}^{Grasper}R(i,1)$ is the first column of the rotation matrix of the Grasper coordinate frame with respect to the Camera coordinate frame.

The error may be calculated as:

$$\Delta = |\cos^{-1}(X_{UID} * X_{Grasper})| \qquad \text{Eqn. 29}$$

The orientation of the robotic tool may be adjusted by using the following:

$$\Delta R_{Grasper} = g_{EulerYPR}(A=\text{yaw}_2, \beta=\text{pitch}_g, \text{yaw}_g) \qquad \text{Eqn. 30}$$

where $\text{yaw}_g, \text{pitch}_g, \text{roll}_g$ are the yaw, pitch and roll of the grasper and where $\beta$ is a coefficient which may be set to speed up or slow down the grasper.

Figure 11D:
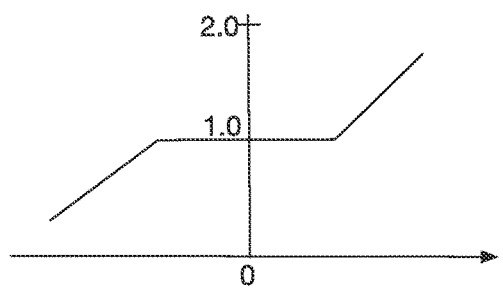
FIG. 11D illustrates a minimized error driving scheme, in accordance with some embodiments.

FIG. 11D illustrates an example of how $\beta$ may be set, in accordance with some embodiments. In this figure the X axis may be set to ($\Delta(t=\tau)-\Delta(t=\tau-d\tau)$). With increasing error the $\beta$ may be set to larger positive values so that the grasper catches up. When the error decreases, $\beta$ is set to smaller values so that the grasper slows down, in some embodiments, when the error is close to 0, $\beta$ may be set to 1. Thus, the groundless UID and the grasper tend to remain in alignment.

Center of Workspace

As described earlier, system 10 provides a groundless UID that the operator may use to control one or multiple robotic tools. Unlike the systems with grounded UIDs, which may provide a console at which the operator may sit or stand, system 10 provides the ability for the operator to move around freely and position himself or herself in an optimal position with respect to the patient. With grounded UIDs, the operator uses the console to orient himself or herself. However, although system 10 may provide a console or a user interface stand, requiring that he or she return to such a console or stand diminishes the advantages of some embodiments the system.

Despite not necessarily having a console or a user interface stand, in some embodiments it may be advantageous to provide a space the operator may return to and is easily accessible to obtain a sense of orientation. This space may be called the center of workspace or a natural workspace. The size and location of the center of workspace may be established in various ways. For example, the center of workspace may be established in relation to the operator, in front of him or her near the torso where the operator's hands can naturally return. Thus, as an example, the center of workspace may be imagined as a virtual sphere about 12 inches in diameter in front of the operator.

Figure 12A:
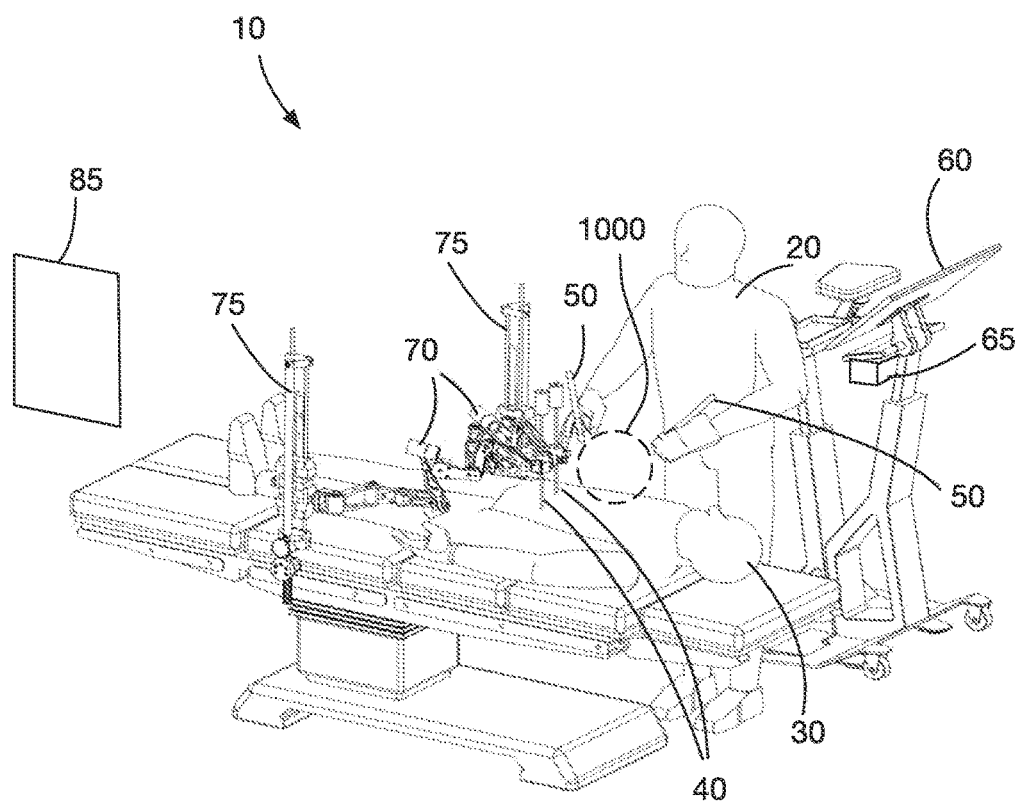
FIGS. 12A, 12B, and 12C illustrate a center of workspace, in accordance with some embodiments.

FIG. 12A illustrates a virtual sphere corresponding to a center of workspace 1000 in front of the operator 20, in accordance with some embodiments. The location of the virtual sphere may be chosen to be static or dynamic. For example, if the location of the sphere is chosen to be static, the location may be established in relation to some physical object such the base of the passive arm 75. Other objects may be chosen as well. On the other hand, if the location of the virtual sphere is chosen to be dynamic, the location may be established in relation to a moving object such as the operator. As stated above, in some embodiments, the virtual sphere may be established in front of the operator near his or her torso. As the operator moves around, the virtual sphere would maintain its location in relation to the operator. This requires that the operator's location be tracked. This tracking may be done in various ways including optical and electromagnetic methods. As an example, the operator may wear a belt with a location sensor located on the belt. In some embodiments, the location sensor may be tracked with the same tracking system that tracks the groundless UIDs.

Figure 12B:
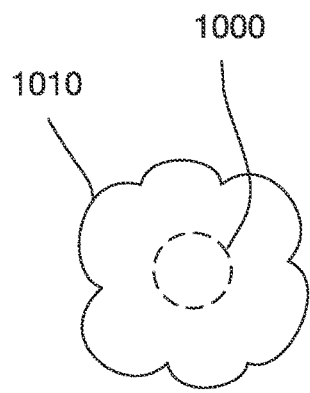
Figure 12C:
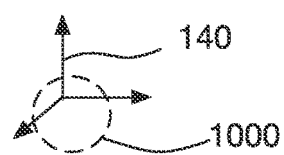

The center of workspace may be used in various ways. In some embodiments, when the operator's hands are anywhere inside the virtual sphere and when the operator engages the drive, a zero position and orientation (hereafter referred to simply as "zero position") for the groundless UID is established. This zero position can thus be made to correspond with the current position of the robotic tool or tools. Once the zero position is established then routine behavior when the system is in a drive state may be followed. FIGS. 12B and 12C illustrate this behavior in accordance with some embodiments. For example, in FIG. 12B, when the system is not in a drive state, the operator may place his or her hand anywhere within the virtual sphere 1000. Within this region after the drive is engaged, that specific location is established as a zero position for the UID coordinate frame 140. This also means that if the operator's hand is outside the virtual sphere 1000, even when the drive is engaged, system 10 disallows driving and sends a message to the operator alerting him or her that the driving action has not occurred. The operator is required to then position his or her hands within the virtual sphere. However if the hands are in the virtual sphere, and the drive is engaged, the specific location of the groundless UID at the instant the drive is engaged is established as a zero position for the duration the drive is engaged. Thus during the course of operating on a patient, the virtual sphere, regardless of whether it is static or dynamic, provides a way to orient the operator. These embodiments may be used with systems that are a normally engaged or a normally unengaged system. In addition, in some embodiments, a secondary drive may be included to provide a safety lock-out that prevents operation unless one or more conditions are met. For example, the system may track the eyes of the operator from the display screen and disallow driving the tools if the eyes are not on the screen. As another example, the system may receive feedback from sensors (for example, pressure sensors or capacitive sensors) on the UIDs and then disallow driving if the operator's hands are not on the UIDs.

Figure 12D:
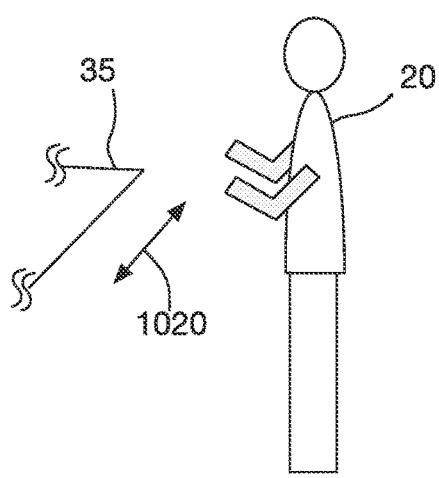
FIGS. 12D and 12E illustrate utilization of the center of workspace, in accordance with some embodiments.
Figure 12E:
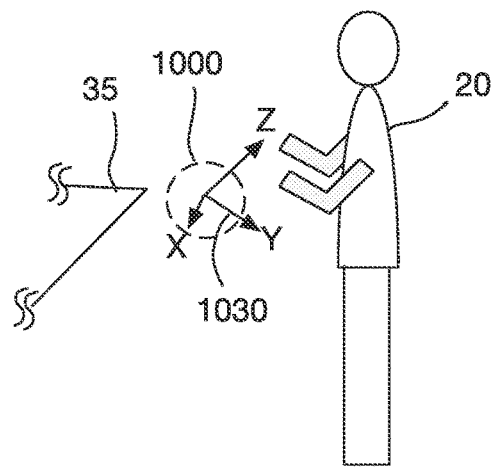

In some embodiments, a natural coordinate frame with respect to the operator may be established. The purpose of this natural coordinate frame is to map the natural movements of the operator to specific movements of the robotic tool or tools. As an example, in FIG. 12D an operator 20 is shown standing near the bed 35. Arrow 1020, which is shown slanted and towards and away from the operator may be a natural way for the operator to move his or her hands. This natural movement may be mapped into a movement of the robotic tool or tools along the camera axis, as illustrated in FIG. 12E, where the center of workspace is shown by a virtual sphere 1000, A coordinate system 1030 with its origin within the sphere is shown such that the Z axis of this coordinate system aligns with the natural direction 1020 of how the operator may move his or her hands. Thus the motion along the Z axis of 1030 may be mapped to the motion of the robotic tool along the camera axis. In other words, if the image of the robotic tool is seen on the screen 85, motion along the Z axis of 1030 may appear as going in and out of the screen. In some embodiments, the orientation of the coordinate frame 1030 may be configurable. As an example, before the start of a procedure or during the set up process, system 10 may instruct the operator to perform certain actions such as move his or her arms up and down. By tracking and recording the position of the arms and the position of the operator's body, the orientation of the coordinate frame may be set. In addition, in some embodiments, this same procedure may be used to establish the location of the center of workspace as well. In some embodiments, the transformations described above with respect to the natural coordinate frame could apply as well to the eye coordinate frame.

In some embodiments, a display (for example, monitor 85) may be used to warn the operator if the groundless UIDs are outside the usable workspace of the robotic system or within a certain distance from an edge of the usable workspace, prompting the operator to return the groundless UIDs to the usable workspace.

Independent Coordinate Frames for Each Hand

When humans move their hands, the movements are interpreted by the brain in complex ways. In some situations, the movement may be understood with reference to an internal coordinate frame of reference. In some cases, the movements may be understood in relation to other coordinate frames; for example movements may be understood in relation to a frame of reference attached to one's forearms, To explain this further with a specific example, a person with an arm outstretched in front of him may move the arm left or right and the brain may understand this motion as a left of right motion in relation to an internal reference frame. However this same person may swing the same arm behind him and may move the arm left or right. Now the brain understands left or right directions in relation to a coordinate frame associated with some part of the arm such as the forearm. In addition. In relation to the earlier internal reference frame, the notion of left and right is reversed. This same experiment may be conducted with the other hand pointing backwards as well. Thus one implication of this thought experiment is that the two hands may move in independent coordinate frames of reference, each coordinate reference frame coupled to some part of the arm. For example, in some embodiments, an operator may use a first hand to control a first UID and a second hand to control a second UID. The first hand and the second hand tray be associated with a first frame of reference and a second frame of reference. In some embodiments, the first and second frames of reference may be the same. In other embodiments, the first and second frames of reference may be different from each other. The first and second frames of references may be orthogonal to each other, or not orthogonal to each other.

Figure 13A:
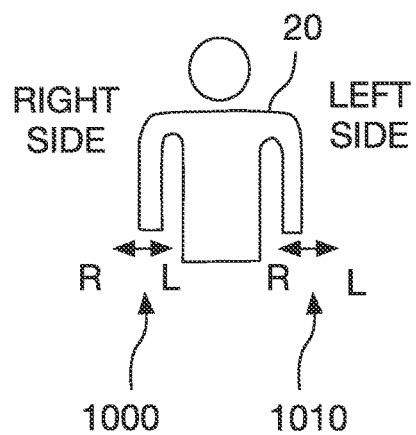
FIG. 13A illustrates the sense of left and right for each arm of an operator, wherein the sense of left and right is coincident with the left and right side for the operator in general, in accordance with some embodiments.
Figure 13B:
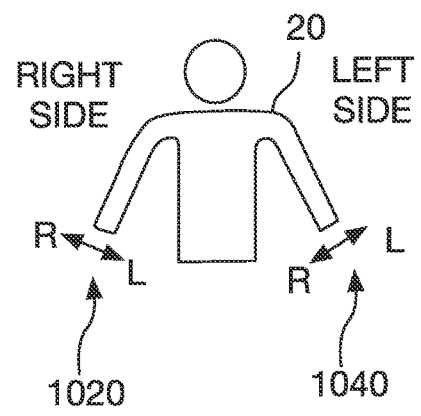
FIG. 13B illustrates the left and right sense of each arm of an operator, wherein the left and right sense are not coincident with the left and right sense of the head or body of the operator, in accordance with some embodiments.

Replicating this behavior of moving the two hands in independent coordinate frames may be advantageous in some embodiments when an operator is controlling system 10 with groundless UIDs. FIGS. 13A and B illustrate independent coordinate flames associated with two hands, in accordance with some embodiments. In FIG. 13A, arrows 1000 and 1010 show the left and right positions of each arm of an operator 20. In some embodiments, the right and left side of each arm may be coincident with the right and left side of the operator as shown. In FIG. 13B, the operator has his arms at an angle; in this case the right and left side of each arm is not coincident with the right and left side of the operator. Arrows 1020 and 1040 show that the right and left side of each arm at an angle in relation to the arrows 1000 and 1010 and in relation to the right and left side of the operator. Further, in some embodiments, the right and left side of each arm may not even be coplanar with each other or with the right side and left side of the operator. Yet, in the situation illustrated in FIG. 13B, it may be advantageous in some embodiments to map the left and right directions of each arm to a left and right direction of the robotic tool as seen by a camera and displayed on a screen.

Thus it may be desirable in some embodiments to allow the manipulation of the groundless UIDs in two independent coordinate frames. This concept is described mathematically below and in FIGS. 14 and 15. In some embodiments, the use of two independent coordinate frames provides increased performance of the system.

Figure 14:
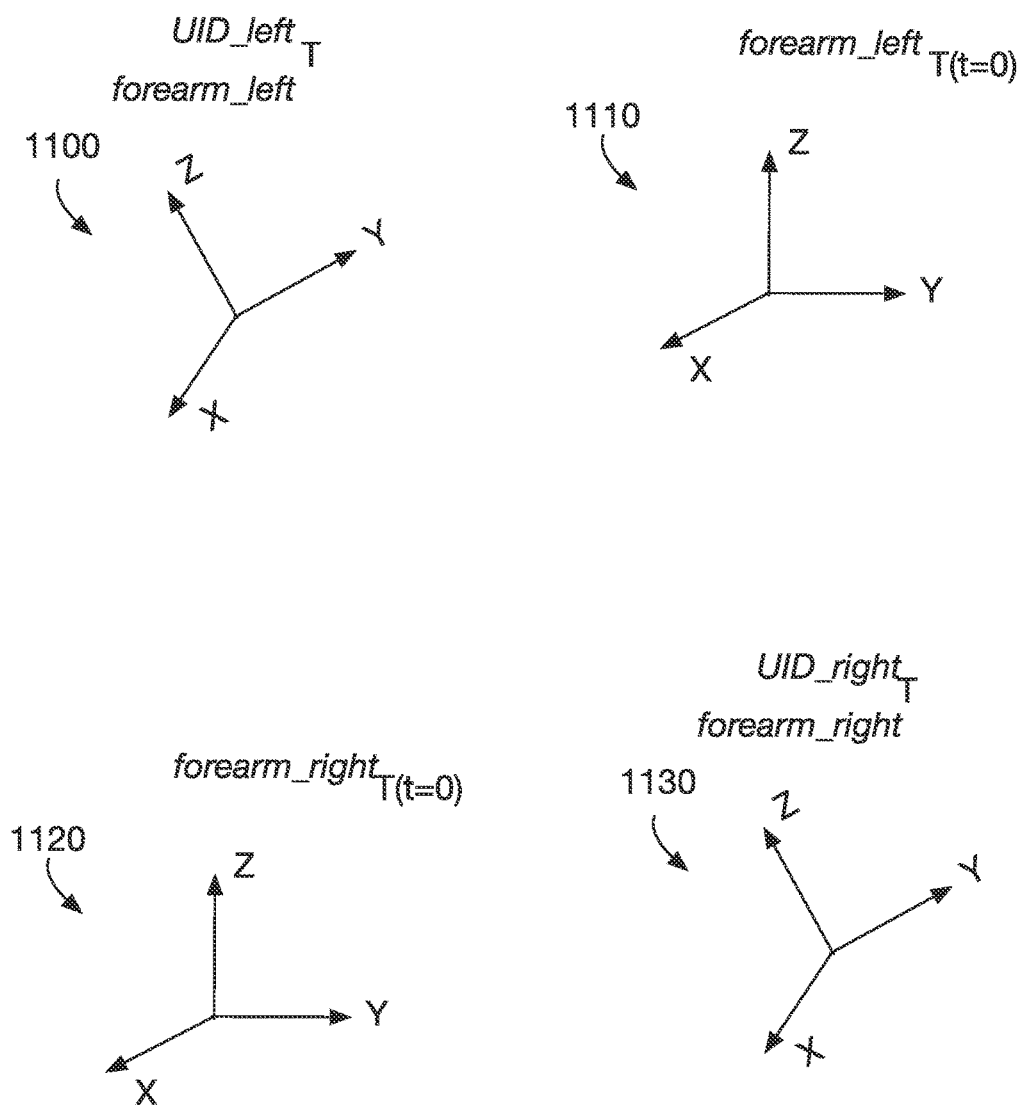
FIG. 14 illustrates two independent coordinate frames, one associated with each arm, in accordance with some embodiments.

FIG. 14 illustrates two independent coordinate frames, one associated with each arm, in accordance with some embodiments. As illustrated in FIG. 14, graphs 1100 and 1110 depict that a UID may be manipulated by the left hand may move in a coordinate frame 1100 associated with the left hand. In some embodiments, this coordinate system may be measured in relation to a coordinate system 1110 that may be associated with the left forearm. As graph 1110 indicates, the coordinate frame associated with the left forearm may be established when the operator engages the drive. In other words, the instantaneous position and orientation of the left forearm when the drive is engaged (al time t=0) may be used as the reference flame for the UID manipulated by the left arm during the drive period.

Similarly, an independent coordinate frame may be established on the right forearm as well, as shown by graph 1120, at the instant the drive is engaged. The coordinate frame associated with the UID held by the right hand 1130, may then be measured in relation to the coordinate frame 1120 associated with the right forearm. In some embodiments, the coordinate frames in the forearms may be tracked by some type of tracking device such as but not limited to an optical tracking device or a magnetic tracking device.

In some embodiments discussed above, regarding the concept of the independent coordinate frames for the two hands, the UID base 65 was used as the device that was used to track the UID devices. In some embodiments where independent coordinate frames are established on the forearms, the same UID base 65 may be used to track the forearms. The forearms or other portion of the operator's body may be equipped with additional instrumentation which is tracked by the base 65, such as magnetic sensors or optically distinguishable features. Hence, the motion of the UID with respect to the forearm it is associated with may be written as:

$$_{forearms(t=0)}^{UID}R = _{UID\ Base}^{Forearm}R^T(T=0)_{UID\ Base}^{UID}R \qquad \text{Eqn. 31}$$

Eqn. 31 is written without the left or right designators but may be applied to both hands.

Figure 15:
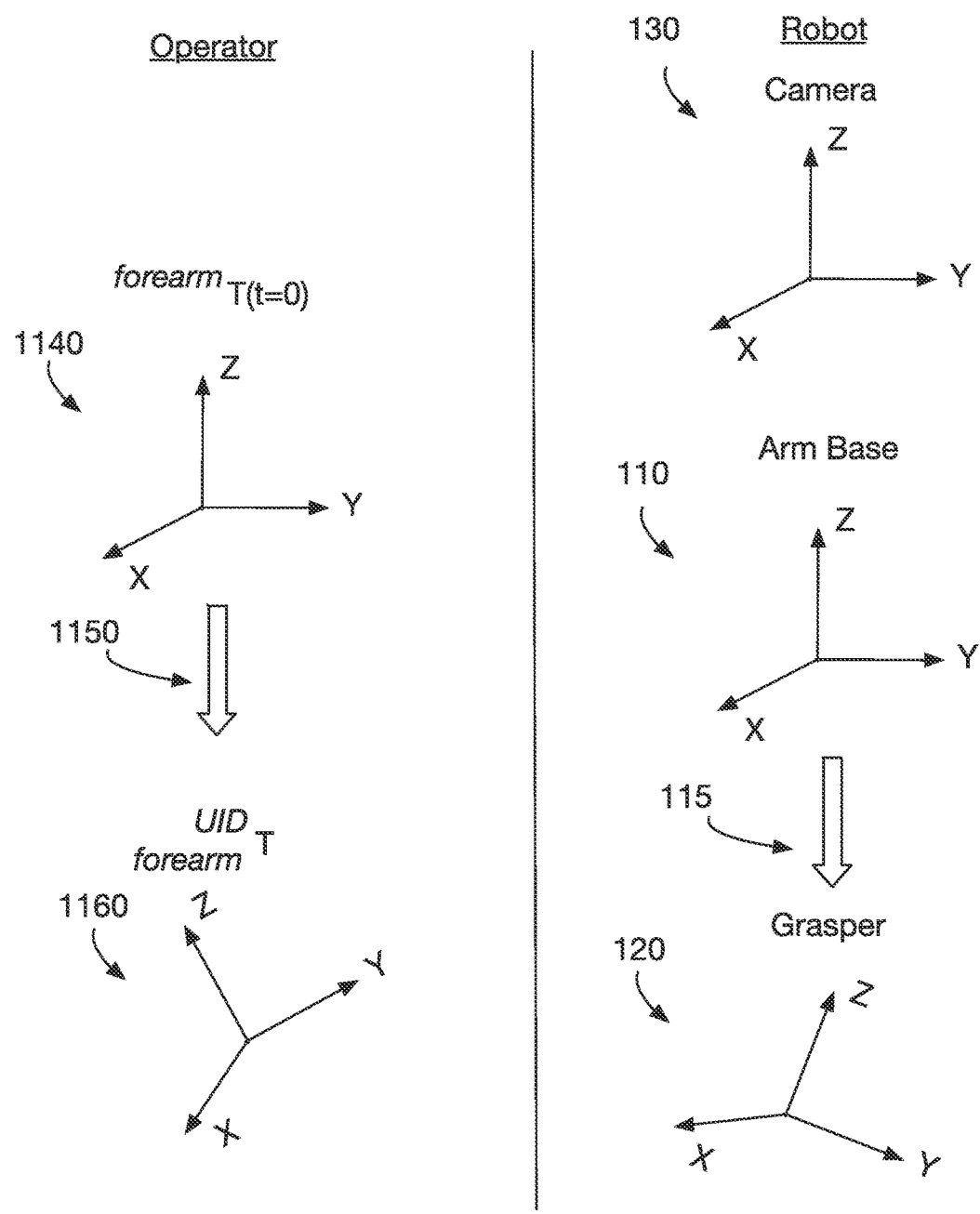
FIG. 15 illustrates a coordinate transformation for the two independent coordinate systems described in FIG. 14, in accordance with some embodiments.

FIG. 15 illustrates a coordinate transformation for two independent coordinate systems, such as those described in FIG. 14, in accordance with some embodiments. Also as stated above, the designators 'left' and 'right' for the left arm and hand and right arm and hand are not used; hence the figure is applicable to each arm and hand with the understanding that the coordinate frames in each forearm may be independent. FIG. 15 is very similar to FIG. 3; in fact the right side or the "Robot" side is identical to the same side in FIG. 3. The difference between FIG. 3 and FIG. 15 is that in FIG. 3, both hands and arms were referenced to one common reference frame, the "UID Base" reference frame. However, in FIG. 15, the frame associated with each hand may be tracked in relation to a coordinate reference system associated with the forearms.

Also as stated above, in accordance with some embodiments, the coordinate frames associated with each forearm may be established at the instant the drive is applied. During the time that the system is in the drive state, the forearms and the associated hands can move around but are measured in relation to the position established when the drive is engaged. In some embodiments, a new coordinate reference frame may be established when the drive is disengaged and reengaged again. Thus, the sense of left and right of the each arm is established at the instant the drive is engaged and with respect to the forearm. Moreover, the sense for each arm may be independent of the sense for the other arm.

Figure 16:
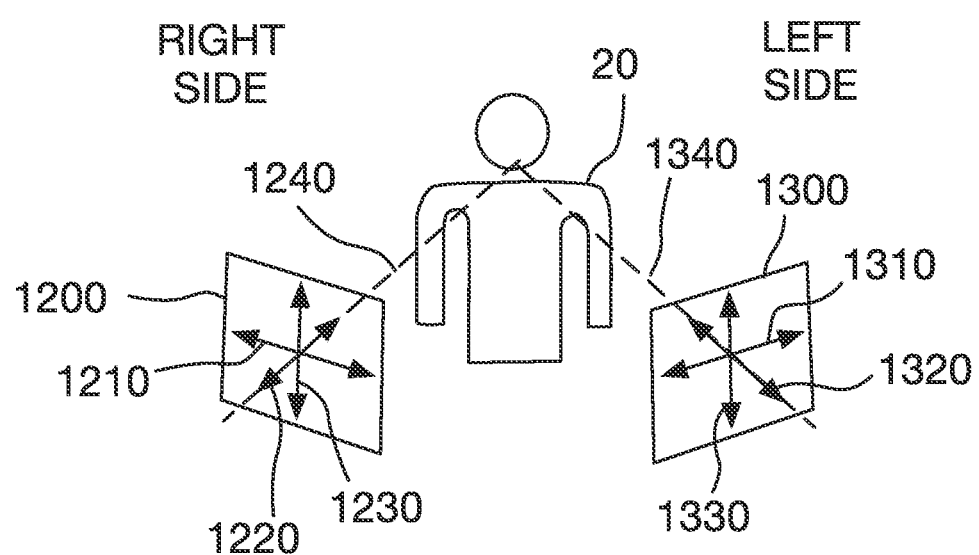
FIG. 16 illustrates two independent coordinate frames, in accordance with some embodiments.

FIG. 16 illustrates two independent coordinate frames, in accordance with some embodiments. As illustrated in FIG. 16, an operator is seen along with two coordinate reference frames 1200 and 1300. The operator may move groundless UIDs in these two planes. In some embodiments, the angle of these two planes may be set independently of each other. For example, the angles may be set at drive engagement time or it may be set at other times.

Referring to plane 1200, moving the groundless UID along arrow 1210 may in some embodiments be translated to right and left motion of the robotic tool when seen via the camera. Similarly, moving the groundless UIDs along arrow 1230 may be translated to up and down motion of the robotic tool also when seen via the camera. Finally in some embodiments, the dashed line 1240 may depict a natural way for the hand to move away from a location on the face such as the mouth, such as described in relation to FIG. 12E. This direction may be mapped into motion of the tool along the camera axis. Thus picking a natural motion of the body to map into an in and out motion of the tool (or movement of the tool along the camera axis) along with a plane that may be perpendicular to the natural motion within which left and right and up and down motions are defined, may increase the ease of use of the robotic system. Similar to plane 1200, plane 1300 illustrates the same motions (for example, up, down, left, right, in and out) but in relation to the left arm.

In some embodiments, if the user Moves the groundless UID along arrow 1210 in the plane 1200, the robotic tool may move left and right as seen by the camera. Independent of this motion, if the user moves a groundless UID along arrow 1310 in plane 1300, a robotic tool may also move left and right as seen by a camera as well. The left and right motion initiated by each hand is applied to the tools regardless of the angle of planes 1200 and 1300. In some embodiments, coordinate frames 1200 and 1300 may change as the operator moves around or changes orientation in the room or as his or her forearm positions change. In some embodiments, updates to coordinate frames 1200 and 1300 may occur continuously (for example, while the drive is engaged). The updates may occur immediately or after a delay. In some embodiments, updates to coordinate frames 1200 and 1300 may happen discretely (for example, at each engage or disengage of the drive), or only upon input or choice by the operator (for example, the operator chooses when to redefine the UID workspace). Thus, if the operator moves, these planes may also move with the operator. This may be advantageous in some embodiments, allowing the operator to manipulate the robot in a convenient and comfortable manner.

Decoupling Coupled Motions With Hardware

Above embodiments of methods were described to decouple the coupled motions of the operator's hands. In some embodiments, the decoupling may be achieved by the use of additional tracking devices. For example, FIG. 17 illustrates a hyperdexterous surgical system having multiple sensors to decouple the coupled motion of the hands of the operator, in accordance with some embodiments.

Figure 17:
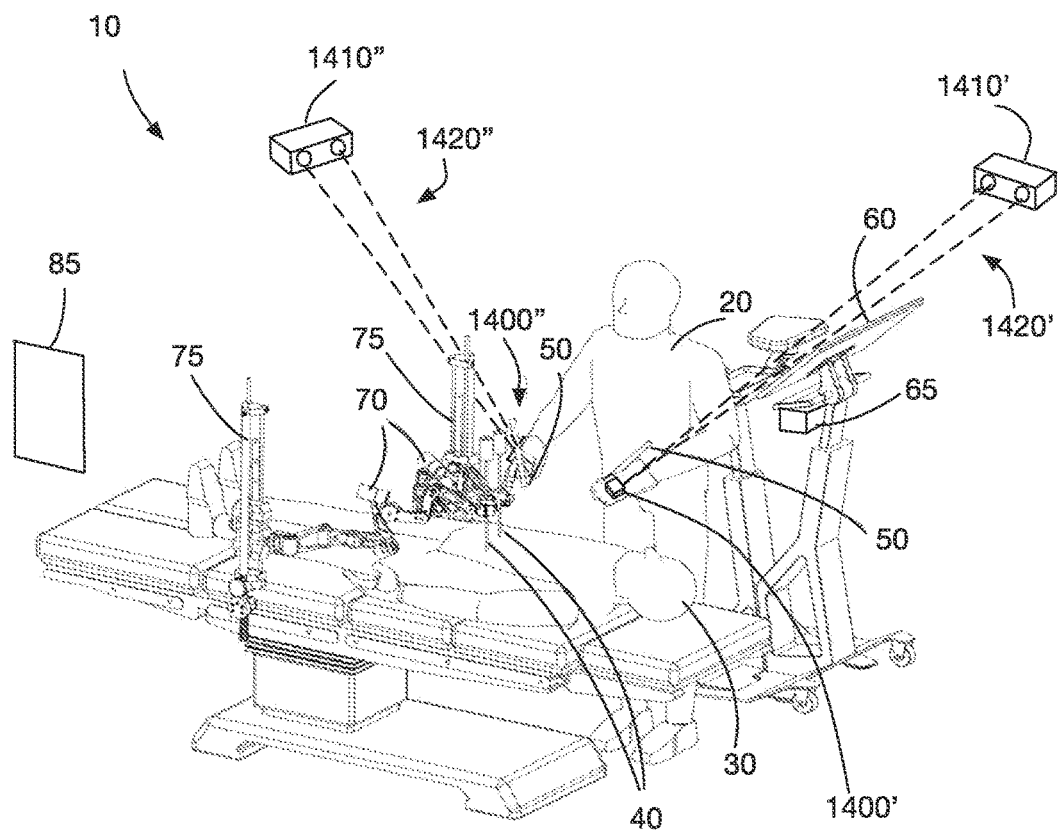
FIG. 17 illustrates a hyperdexterous surgical system having multiple sensors to decouple the coupled motion of the hands of the operator, in accordance with some embodiments.

As illustrated in FIG. 17, the operator 20 is seen operating the system 10 with groundless UIDs 50. The operator can also be seen coupled to devices 1400' and 1400". In some embodiments, these devices are situated on the back of the palms of the operator. In other embodiments, these devices may be situated at some other location along the operator's arm. In some embodiments, devices 1400' and 1400" may comprise one or more sensors (for example, sensors for magnetic tracking, sensors for inertial sensing, and/or the like). In other embodiments, such as those that use optical tracking, devices 1400' and 1400" may not contain any sensors, and may instead comprise one or more lights and/or reflective surfaces.

Also seen in the figures are two cameras 1410' and 1410". In some embodiments, camera 1410' is seen to have a direct line of sight to device 1400' and camera 1410" is seen to have a direct line of sight to device 1400". Devices 1400' and 1400" may have reflective surfaces, lights, pins or balls which along with the cameras 1400' and 1410" form the optical tracking system. Thus camera 1410' and device 1400' may track the position of the left hand of the operator 20 whereas camera 1410" and device 1400" may track the position of the right hand of the operator. Although devices 1400' and 1400" are illustrated at the back of the operator's hand, other locations may be chosen (for example, on groundless UIDs 50, or on other locations of the operator's body). In some embodiments, the locations of devices 1400' and 1400" and cameras 1410' and 1410" may be reversed (for example, the cameras are located on the back of the operator's hand, while the devices are mounted with direct line of sight to the cameras). In Wale embodiments, other types of sensors may be utilized, such as magnetic tracking systems or visual tracking systems which are configured to recognize the shape of the operator's hand rather than a particular device or instrument affixed to the hand or body of the operator. Additionally, inertial sensing may be used (such as accelerometers), which would not require the presence of external tracking devices such as 1410' and 1410".

With this embodiment, the coupled translatory motion that the groundless UIDs may be subject to when the operator rolls the UID with his or her fingers, may be decoupled and reduced or eliminated when the motion of the UID is applied to the motion of the end-effectors. To explain this further, if the operator rolls the groundless UID 50 (in some embodiments, it is immaterial if one or both hands are used) for example to apply a stitch to tissue, from the above discussion, it is expected that some translatory motion may couple into the groundless UID. However using the supplemental tracking system described above or other tracking systems, the translatory motion can be measured. Assuming that the tracking system measures the same translatory motion that the groundless UID experiences, then the coupled translatory motion can be removed or eliminated from the motion applied to the end-effectors. In mathematical terms, if the motion of any one of the UIDs is depicted by $_{UID\ base}{}^{UID}T$, then if the UID experiences a roll and a translatory motion, in some embodiments it may be written as:

$$_{UID\ base}{}^{UID}T = \begin{bmatrix} _{UID\ Base}{}^{UID}R & _{UID\ Base}{}^{UID}P \\ 0 & 1 \end{bmatrix} \quad \text{Eqn. 32}$$

The devices 1400' and 1400" may not experience any rolling motion when the groundless UID is subject to rolling motion by the operator using his or her fingers although it may experience the same translatory motion. It may also experience a motion which is mathematically related to the translatory motion of the groundless by a function determined by the kinematics of the human hand. Thus, assuming that the translatory motion of the groundless UID is the same as the translator motion of the sensors on the back of the palm, the following equation may be written as:

$$_{UID\ Base}{}^{UID}P = _{sensor\_base}{}^{back\_sensor}P \quad \text{Eqn. 33}$$

where $_{UID\ Base}{}^{UID}P$ denotes the translatory motion of the groundless UID and $_{sensor\_base}{}^{back\_sensor}P$ denotes the translatory motion of the sensors 1400' or 1400". Now, the final applied motion of the robotic tool may be written as some general function φ of the two parameters: the motion of the UID (which has coupled motion) and the motion of the sensors in the back of the palm. Thus, $$_{Arm\ base}{}^{Grasper}M_{Final} = \varphi(_{UID\ Base}{}^{UID}T, _{UID\ Base}{}^{UID}P) \quad \text{Eqn. 34}$$

As specified in Eqn. 33, the translatory motion of the groundless UID is the same as the translatory motion of the device on the back of the palm. While calculating the final output in Eqn. 34, this component can be eliminated. Thus having an independent device that experiences only the translatory motion, allows decoupling of this motion from the groundless UID motion.

In some embodiments, while two cameras 1410' and 1410" are illustrated in FIG. 17, only one camera may be needed. Other embodiments may include using sensors that are not optical in nature. Thus sensors 1400' and 1400" may be of various types including but not limited to electromagnetic sensors. In addition, while the illustration of the groundless UIDs in the figure looks like a long tubular structure, it is understood that in other embodiments, other shapes are possible.

It can be thus seen that with the above concepts, a method for orientation may be provided. In addition, a method to map the operator's natural motions to specific motions of the robotic tool is provided. Embodiments of these methods may advantageously improve the ease of use of system 10.

Implementation Mechanisms

According to an embodiment, the hyperdexterous system user interface and other methods and techniques described herein may be implemented by one or more special-purpose computing devices. The special-purpose computing devices may be hard-wired to perform the techniques, or may include digital electronic devices such as one or more application-specific integrated circuits (ASICs) or field programmable gate arrays (FPGAs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. The special-purpose computing devices may be desktop computer systems, server computer systems, portable computer systems, handheld devices, networking devices or any other device or combination of devices that incorporate hard-wired and/or program logic to implement the techniques.

Computing device(s) are generally controlled and coordinated by operating system software, such as iOS, Android, Chrome OS, Windows XP, Windows Vista, Windows 7, Windows 8, Windows Server, Windows CE, Unix, Linux, SunOS, Solaris, iOS, Blackberry OS, VxWorks, or other compatible operating systems. In other embodiments, the computing device may be controlled by a proprietary operating system. Conventional operating systems control and schedule computer processes for execution, perform memory management, provide file system, networking, I/O services, and provide a user interface functionality, such as a graphical user interface ("GUI"), among other things.

For example, FIG. 18 is a block diagram that illustrates an embodiment of a computer system 1800 upon which the various systems and methods discussed herein may be implemented. For instance, a computer system associated with system 10 as described above may be implemented as one or more computer systems 1800 or servers 1830 as illustrated in FIG. 18.

Computer system 1800 includes a bus 1802 or other communication mechanism for communicating information, and a hardware processor, or multiple processors, 1804 coupled with bus 1802 for processing information. Hardware processor(s) 1804 may be, for example, one or more general purpose microprocessors.

Computer system 1800 also includes a main memory 1806, such as a random access memory (RAM), cache and/or other dynamic storage devices, coupled to bus 1802 for storing information and instructions to be executed by processor 1804. Main memory 1806 also may be used for storing temporary variables or other intermediate information during execution of instructions to be executed by processor 1804. Such instructions, when stored in storage media accessible to processor 1804, render computer system 1800 into a special-purpose machine that is customized to perform the operations specified in the instructions.

Computer system 1800 further includes a read only memory (ROM) 1808 or other static storage device coupled to bus 1802 for storing static information and instructions for processor 1804. A storage device 1810, such as a magnetic disk, optical disk, or USB thumb drive (Flash drive d/or any other suitable data store, is provided and coupled to bus 1802 for storing information and instructions, such as sensor data, robotic tool control instructions, and/or the like.

Computer system 1800 may be coupled via bus 1802 to a display 1812, such as a cathode ray tube (CRT), LCD display, or touch screen display, for displaying information to a user and/or receiving input from the user. For example, monitor 85, as illustrated in FIG. 1, may be implemented as a display 1812. An input device 1814, which may include alphanumeric and other keys, is coupled to bus 1802 for communicating information and command selections to processor 1804. Another type of user input device is cursor control 1816, such as a mouse, a trackball, or cursor direction keys for communicating direction information and command selections to processor 1804 and for controlling cursor movement on display 1812. This input device typically has at least two degrees of freedom in two axes, a first axis (for example, x) and a second axis (for example, y), that allows the device to specify positions in a plane. In some embodiments, the same direction information and command selections as cursor control may be implemented via receiving touches on a touch screen without a cursor. In some embodiments, UIDs 50, as illustrated in FIG. 1, may be implemented as input device 1812 and/or cursor control 1816, Computing system 1800 may include a user interface module, and/or various other types of modules to implement one or more graphical user interface of the data analysis system, as described above. The modules may be stored in a mass storage device as executable software codes that are executed by the computing device(s). This and other modules may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables.

In general, the word "module," as used herein, refers to a collection of software instructions, possibly having entry and exit points, written in a programming language, such as, for example, Java, Lua, C or C++. A software module may be compiled and linked into an executable program, installed in a dynamic link library, or may be written in an interpreted programming language such as, for example, BASIC, Perl, or Python. It will be appreciated that software modules may be callable from other modules or from themselves, and/or may be invoked in response to detected events or interrupts. Software modules configured for execution on computing devices may be provided on a computer readable medium, such as a compact disc, digital video disc, flash drive, magnetic disc, or any other tangible medium, or as a digital download (and may be originally stored in a compressed or installable format that requires installation, decompression or decryption prior to execution). Such software code may be stored, partially or fully, on a memory device of the executing computing device, for execution by the computing device. Software instructions may be embedded in firmware, such as an EPROM. It will be further appreciated that hardware devices (such as processors and CPUs) may be comprised of connected logic units, such as gates and flip-flops, and/or may be comprised of programmable units, such as programmable gate arrays or processors. Generally, the modules described herein refer to logical modules that may be combined with other modules or divided into sub-modules despite their physical organization or storage. In various embodiments, aspects of the methods and systems described herein may be implemented by one or more hardware devices, for example, as logic circuits, in various embodiments, some aspects of the methods and systems described herein may be implemented as software instructions, while other may be implemented in hardware, in any combination.

As mentioned, computer system 1800 may implement the techniques described herein using customized hard-wired logic, one or more ASICs or FPGAs, firmware and/or program logic which in combination with the computer system causes or programs computer system 1800 to be a special-purpose machine. According to one embodiment, the techniques herein are performed by computer system 1800 in response to processor(s) 1804 executing one or more sequences of one or more modules and/or instructions contained in main memory 1806. Such instructions may be read into main memory 1806 from another storage medium, such as storage device 1810. Execution of the sequences of instructions contained in main memory 1806 causes processor(s) 1804 to perform the process steps described herein. In alternative embodiments, hard-wired circuitry may be used in place of or in combination with software instructions.

The term "non-transitory media," and similar terms, as used herein refers to any media that store data and/or instructions that cause a machine to operate in a specific fashion. Such non-transitory media may comprise non-volatile media and/or volatile media. Non-volatile media includes, for example, optical or magnetic disks, such as storage device 1810. Volatile media includes dynamic memory, such as main memory 1806. Common forms of non-transitory media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge, and networked versions of the same.

Non-transitory media is distinct from but may be used in conjunction with transmission media. Transmission media participates in transferring information between non-transitory media. For example, transmission media includes coaxial cables, copper wire and fiber optics, including the wires that comprise bus 1802. Transmission media can also take the form of acoustic or light waves, such as those generated during radio-wave and infra-red data communications.

Various forms of media may be involved in carrying one or more sequences of one or more instructions to processor 1804 for execution. For example, the instructions may initially be carried on a magnetic disk or solid state drive of a remote computer. The remote computer can load the instructions and/or modules into its dynamic memory and send the instructions over a telephone line using a modem. A modem local to computer system 1800 can receive the data on the telephone line and use an infra-red transmitter to convert the data to an infra-red signal. An infra-red detector can receive the data carried in the infra-red signal and appropriate circuitry can place the data on bus 1802. Bus 1802 carries the data to main memory 1806, from which processor 1804 retrieves and executes the instructions. The instructions received by main memory 1806 may optionally be stored on storage device 1810 either before or after execution by processor 1804.

In some embodiments, Computer system 1800 may also include a communication interface 1818 coupled to bus 1802. Communication interface 1818 provides a two-way data communication coupling to a network link 1820 that is connected to a local network 1822. For example, communication interface 1818 may be an integrated services digital network (ISDN) card, cable modem, satellite modem, or a modem to provide a data communication connection to a corresponding type of telephone line. As another example, communication interface 1818 may be a local area network (LAN) card to provide a data communication connection to a compatible LAN (or WAN component to communicate with a WAN). Wireless links may also be implemented. In any such implementation, communication interface 1818 sends and receives electrical, electromagnetic or optical signals that carry digital data streams representing various types of information.

Network link 1820 typically provides data communication through one or more networks to other data devices. For example, network link 1820 may provide a connection through local network 1822 to a host computer 1824 or to data equipment operated by an Internet Service Provider (ISP) 1826. ISP 1826 in turn provides data communication services through the world wide packet data communication network now commonly referred to as the "Internet" 1828. Local network 1822 and Internet 1828 both use electrical, electromagnetic or optical signals that carry digital data streams. The signals through the various networks and the signals on network link 1820 and through communication interface 1818, which carry the digital data to and from computer system 1800, are example forms of transmission media.

Computer system 1800 can send messages and receive data, including program code, through the network(s), network link 1820 and communication interface 1818. In the Internet example, a server 1830 might transmit a requested code for an application program through Internet 1828, ISP 1826, local network 1822 and communication interface 1818. For example, in an embodiment various aspects of the data analysis system may be implemented on one or more of the servers 1830 and may be transmitted to and from the computer system 1800. For example, data may be transmitted between computer system 1800 and one or more servers 1830. In an example, sensor data may be transmitted to one or more servers 1830, and analysis data, such as robotic tool control instructions, may then be transmitted back from servers 1830.

Additional Embodiments

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Any process descriptions, elements, or blocks in the flow diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

The methods and tasks described herein may be performed and fully automated by a computer system. The computer system may, in some cases, include multiple distinct computers or computing devices (for example, physical servers, workstations, storage arrays, and so forth) that electronically communicate and interoperate over a network to perform the described functions. Each such computing device typically includes a processor (or multiple processors) that executes program instructions or modules stored in a memory or other computer-readable storage medium. Where the system includes multiple computing devices, these devices may, but need not, be co-located. The results of the disclosed methods and tasks may be persistently stored by transforming physical storage devices, such as solid state memory chips and/or magnetic disks, into a different state.

The methods and processes described above may be embodied in, and fully automated via, software code modules executed by one or more general purpose computers. The code modules may be stored in any type of computer-readable medium or other computer storage device. Some or all of the methods may alternatively be embodied in specialized computer hardware. The results of the disclosed methods may be stored in any type of computer data repository, such as relational databases and flat file systems that use magnetic disk storage and/or solid state RAM.

Many variations and modifications may be made to the above-described embodiments, the elements of which are to be understood as being among other acceptable examples. All such modifications and variations are intended to be included herein within the scope of this disclosure. The foregoing description details certain embodiments of the invention. It will be appreciated, however, that no matter how detailed the foregoing appears in text, the invention can be practiced in many ways. As is also stated above, the use of particular terminology when describing certain features or aspects of the invention should not be taken to imply that the terminology is being re-defined herein to be restricted to including any specific characteristics of the features or aspects of the invention with which that terminology is associated.

What is claimed is:

1. A system comprising: a first robotic tool;
a first groundless user interface device (UID) for use by an operator configured to control the first robotic tool using a first frame of reference, the control comprising:
identifying a first UID motion of the first UID;
comparing an orientation of the first UID with respect to a first coordinate frame with an orientation of the first robotic tool with respect to a second coordinate frame to determine whether the orientation of the first UID with respect to the first coordinate frame is within a certain region relative to the first robotic tool with respect to the second coordinate frame,
wherein the first UID controls the first robotics tool if the orientation of the first UID with respect to the first coordinate frame is within the certain region relative to the first robotic tool with respect to the second coordinate frame, and the certain region comprises a cone around the first robotic tool, the cone comprising a vertex corresponding to an end of the first robotic tool and a cone angle that is modifiable depending on a type of the first robotic tool,
and
performing a first robotic tool movement of the first robotic tool based at least in part upon the identified first UID motion of the first UID.

2. The system of claim 1 further comprising a second robotic tool and a second groundless user interface device (UID) for use by the operator configured to control the second robotic tool using a second frame of reference independent of the first frame of reference, the control comprising:
identifying a second UID motion of the second UID; and
performing a second robotic tool movement of the second robotic tool based at least in part upon the identified second UID motion of the second UID.

3. The system of claim 1, wherein the first robotic tool comprises at least one of a grasper, a surgical tool, or a camera.

4. The system of claim 2, wherein the first UID is further configured to be controlled by a first hand of the operator and the second UID is further configured to be controlled by a second hand of the operator.

5. The system of claim 3, wherein controlling the first tool further comprises:
determining that a drive has been engaged; and
in response to determining that the drive has been engaged, establishing a position on a first forearm of the operator associated with the first hand, wherein a UID motion of the first UID is measured in relation to the position on the first forearm.

6. The system of claim 1, wherein the first coordinate frame corresponds to a natural coordinate frame associated with the operator, and the second coordinate frame corresponds to a camera frame associated with the first robotic tool.

7. The system of claim 1, wherein a speed of the first robotic tool movement of the first robotic tool is adjusted based at least in part upon a calculated difference between the orientation of the first UID relative to the first robotic tool.

8. The system of claim 1, wherein the first robotic tool is associated with a plurality of control schemes associated with a plurality of different regions, and wherein one of the plurality of control schemes used by the first UID to control the first robotic tool is based at least in part upon the orientation of the first UID with respect to the first coordinate frame relative to the orientation of the first robotic tool with respect to the second coordinate frame.

9. A system
comprising: a first robotic tool;
and
a first groundless user interface device (UID) configured to control the first robotic tool using a first frame of reference, the control comprising:
identifying a first UID motion of the first UID;
decoupling the first UID motion into two or more components comprising a first component and a second component;
performing a first transformation on the two or more components, wherein the first component and the second component are transformed differently; and
performing a first robotic tool movement of the first robotic tool based at least in part upon the first transformation wherein the first UID comprises a UID configured to be held by an operator, such that a position of the UID is based at least in part upon a wrist position of the operator,
a range of motion of the wrist of the operator being partitioned into at least a comfortable region and an uncomfortable region, and wherein the first transformation is based at least in part upon which region the wrist is in.

10. The system of claim 9, wherein the two or more components comprise at least a roll component, a pitch component, and a yaw component, and the first transformation comprises transforming the roll component to the performed first robotic tool movement of the first robotic tool, but not the pitch component or the yaw component, in response to a determination that the identified first UID motion satisfies an established criteria.

11. The system of claim 9, wherein the two or more components comprise at least a roll component, a pitch component, and a yaw component, and the first transformation comprises:
performing an intermediate transformation on the yaw component and the pitch component, wherein the intermediate transformation generates at least a modified yaw component, and a modified pitch component; and
determining a modified roll component,
wherein the first robotic tool movement of the first robotic tool is based at least in part upon one of the modified roll component, modified yaw component, or modified pitch component.

12. The system of claim 9, wherein the two or more components comprises at least a rotational component and a translational component, and wherein the first transformation comprises:
automatically determining whether the translational component satisfies a threshold, and setting a translational component for the first robotic tool movement of the first robotic tool to 0, if the translational component does not satisfy the threshold; and
automatically determining whether the rotational component satisfies a threshold, and setting a rotational component for the first robotic tool movement of the first robotic tool to 0, if the rotational component does not satisfy the threshold.

13. The system of claim 9, wherein the first transformation comprises scaling at least one component of the two or more components, and wherein an amount of scaling is based at least in part upon whether the wrist is in the comfortable region or the uncomfortable region.

14. The system of claim 9, wherein the first UID controls the first robotic tool only if the first UID is located within a natural workspace region.

15. The system of claim 14, wherein controlling the first robotic tool further comprises:
determining that a drive has been engaged;
determining that the first UID is within the natural workspace region; and in
response to determining that the drive has been engaged and that the first UID is within the natural workspace, establishing a zero position for the first UID corresponding to a position of the first robotic tool.

16. A computer-implemented method comprising:
as implemented by one or more computing devices configured with specific computer-executable instructions,
identifying a motion of at least one groundless user interface (UID);
decoupling the identified motion into two or more components, comprising at least a first component and a second component;
performing at least one transformation on the two or more components, wherein the first component and the second component are transformed differently;
comparing an orientation of the at least one UID with an orientation of the at least one robotic tool in a particular coordinate frame,
wherein the at least one UID controls the at least one robotics tool if the orientation of the least one UID is within a certain region relative to the at least one robotic tool in the coordinate frame, and the certain region comprises a cone around the first robotic tool, the cone comprising a vertex corresponding to an end of the first robotic tool,
and
performing a movement of at least one robotic tool, wherein the movement is based at least in part upon the at least one transformation performed on the two or more components.

17. The computer-implemented method of claim 16, wherein the at least one robotic tool comprises at least one of a grasper, a surgical tool, or a camera.

18. The computer-implemented method of claim 16, wherein the at least one UID comprises a first UID and a second UID, the first and second UIDs configured to be controlled by a first hand and a second hand of an operator, and wherein the first and second UIDs may be moved by the first and second hands in independent coordinate frames.

19. The computer-implemented method of claim 16, further comprising:
comparing an orientation of the at least one UID with an orientation of the at least one robotic tool in a particular coordinate frame,
wherein the at least one UID controls the at least one robotics tool if the orientation of the least one UID is within a certain region relative to the at least one robotic tool in the coordinate frame.

20. The computer-implemented method of claim 16, wherein a speed of the movement of the at least one robotic tool is adjusted based at least in part upon a calculated difference between the orientation of the at least one UID relative to the at least one robotic tool.

21. The system of claim 1, wherein the cone angle is modifiable between a first cone angle and a second cone angle, wherein the first cone angle is smaller than the second cone angle.

22. The system of claim 21, wherein the cone angle is the first cone angle when the first robotic tool is a grasper or a stapler and the cone angle is the second cone angle when the first robotic tool is a robotic camera.

\* \* \* \* \*